(12) United States Patent
Adjaoute

(10) Patent No.: US 9,779,407 B2
(45) Date of Patent: Oct. 3, 2017

(54) HEALTHCARE FRAUD PREEMPTION

(71) Applicant: Brighterion, Inc., San Francisco, CA (US)

(72) Inventor: Akli Adjaoute, Mill Valley, CA (US)

(73) Assignee: Brighterion, Inc., San Francisco, CA (US)

( * ) Notice: Subject to any disclaimer, the term of this patent is extended or adjusted under 35 U.S.C. 154(b) by 540 days.

(21) Appl. No.: 14/454,749

(22) Filed: Aug. 8, 2014

(65) Prior Publication Data

US 2015/0081324 A1    Mar. 19, 2015

(51) Int. Cl.
| | |
|---|---|
| G06Q 50/00 | (2012.01) |
| G06Q 30/00 | (2012.01) |
| G06Q 40/08 | (2012.01) |
| G06Q 50/22 | (2012.01) |

(52) U.S. Cl.
CPC ......... *G06Q 30/0185* (2013.01); *G06Q 40/08* (2013.01); *G06Q 50/22* (2013.01)

(58) Field of Classification Search
CPC ...... G06Q 50/22; G06Q 30/015; G06Q 40/08; G06F 19/00; G06F 19/345; G06F 19/3487; G06N 3/0472; G06N 99/005; G06N 7/005; G06K 9/6228; H04W 12/12
USPC .......................................................... 705/3
See application file for complete search history.

(56) References Cited

U.S. PATENT DOCUMENTS

| | | | |
|---|---|---|---|
| 5,819,226 A | 10/1998 | Gopinathan | |
| 6,272,479 B1 | 8/2001 | Farry | |
| 6,330,546 B1 | 12/2001 | Gopinathan | |
| 7,668,769 B2 | 2/2010 | Baker | |
| 7,813,937 B1 | 10/2010 | Pathria | |
| 7,853,469 B2 | 12/2010 | Maitland | |
| 8,027,439 B2 | 9/2011 | Zoldi | |
| 8,041,597 B2 | 10/2011 | Li | |
| 8,090,648 B2 | 1/2012 | Zoldi | |
| 8,548,137 B2 | 10/2013 | Zoldi | |

(Continued)

OTHER PUBLICATIONS

Bonabeau ("Agent-Based modeling: Methods and Techniques for Simulating Human Systems").*

(Continued)

*Primary Examiner* — Michelle L Le
(74) *Attorney, Agent, or Firm* — Louis Wu

(57) ABSTRACT

Real-time fraud prevention software-as-a-service (SaaS) products include computer instruction sets to enable a network server to receive medical histories, enrollments, diagnosis, prescription, treatment, follow up, billings, and other data as they occur. The SaaS includes software instruction sets to combine, correlate, categorize, track, normalize, and compare the data sorted by patient, healthcare provider, institution, seasonal, and regional norms. Fraud reveals itself in the ways data points deviate from norms in nonsensical or inexplicable conduct. The individual behaviors of each healthcare provider are independently monitored, characterized, and followed by self-spawning smart agents that can adapt and change their rules as the healthcare providers evolve. Such smart agents will issue flags when their particular surveillance target is acting out of character, outside normal parameters for them. Fraud controls can therefore be much tighter than those that have to accommodate those of a diverse group.

5 Claims, 9 Drawing Sheets

(56) References Cited

U.S. PATENT DOCUMENTS

2003/0158751 A1* 8/2003 Suresh ................ G06Q 30/02
705/2
2007/0124246 A1 5/2007 Lawyer
2013/0204755 A1 8/2013 Zoldi

OTHER PUBLICATIONS

"10 popular health care provider fraud schemes" by Charles Piper, Jan./Feb. 2013, FRAUD Magazine, www.fraud-magazine.com.
Report to the Nations on Occupational Fraud and Abuse, 2012 Global Fraud Study, copyright 2012, 76 pp., Association of Certified Fraud Examiners, Austin, TX.
Big Data Developments in Transaction Analytics, Scott Zoldi, Credit Scoring and Credit Control XIII Aug. 28-30, 2013, Fair Isaacs Corporation (FICO).
Report to the Congress on Reductions of Consumer Credit Limits Based on Certain Information as to Experience or Transactions of the Consumer, May 2010, 72 pp., Board of Governors of the Federal Reserve System.
Credit card fraud detection using artificial neural networks tuned by genetic algorithms, Dissertation: Carsten A. W. Paasch, Copyright © 2013 Proquest, LLC.
Falcon Fraud Manager, Fair Isaac, Minneapolis, MN, Copyright © 2004, 1247PS Sep. 2004 PDF.
FICO® Falcon® Fraud Manager Stops Payment Fraud, Fair Isaacs Corporation, (c) 2013.
Fraud Detection Using Data Analytics in the Healthcare Industry, Discussion Whitepaper, ACL Services Ltd., (c) 2014, 8 pp.
Fraud Detection of Credit Card Payment System by Genetic Algorithm, K.RamaKalyani, D.UmaDevi Department of Computer Science, Sri Mittapalli College of Engineering, Guntur, AP, India., International Journal of Scientific & Engineering Research vol. 3, Issue 7, Jul. 1, 2012, ISSN 2229-5518.
Healthcare Fraud Detection, http://IJINIIW.21ct.com'solutions/healthcare-fraud-detection/, (c) 2013 21CT, Inc.
Chapter 3: Medicare Fraud & Abuse, SMP Foundations Training: Volunteer Manual.
Fraud and Abuse, Chapter 14, Summer 2014, DME MAC Jurisdiction C Supplier Manual.
Unleash Your Data: Investigative Analytics and Pattern Detection for Intelligence Analysis, LYNXeon™ from 21CT, © 2013, 21CT, Inc., Corporate Headquarters, 6011 W. Courtyard Drive, Building 5, Suite 300, Austin, TX 78730.
The Benefits of Non Algorithmic Programming, NonAlgorithmic Technology 1/17 by Dr. Akli Adjaoute, http://frostiebek.free.fr/docs/Frames%20+%20Blackboard/NonAlgorithmic_Technology_By_Dr_Akli_Adjaoute.pdf.
Handbook of E-Business, Editor Jessica Keyes, Jun. 2000, New Art Technologies, RIAIWG&L Boston> New York.
Managed Healthcare Fraud Detection, © 2009 Scianta Analytics, LLC, Spotlight SS-006 Oct. 18, 2009, Rev: SS-006b Oct. 1, 2012, www.sciantaanalytics.com.
IPrevent Real-time fraud prevention, brochure, Brighterion, Inc. San Francisco, CA.

* cited by examiner

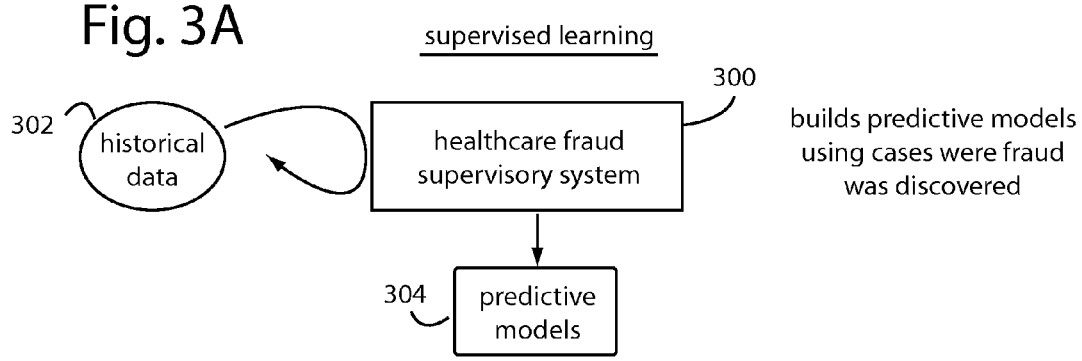
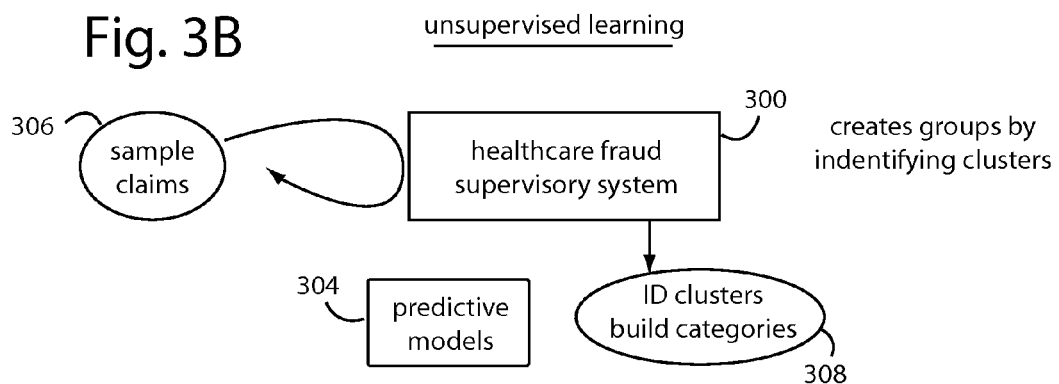
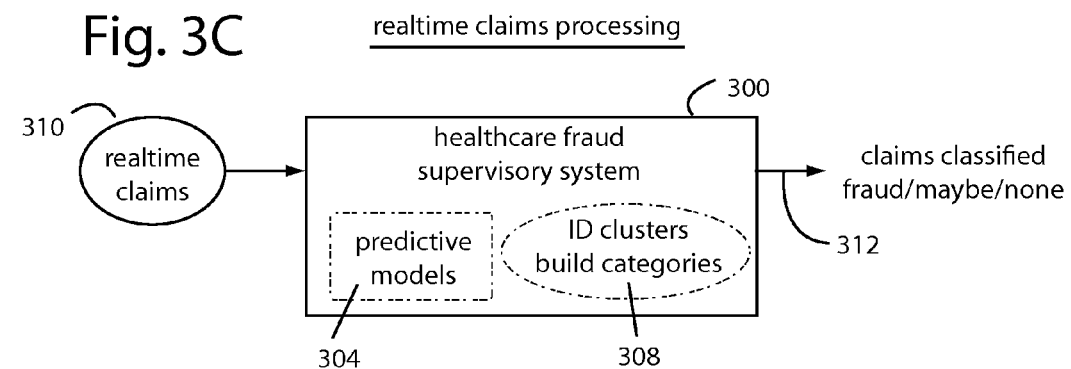

HEALTHCARE FRAUD PREEMPTION

BACKGROUND OF THE INVENTION

Field of the Invention

The present invention relates to healthcare fraud preemption, and more particularly to real-time computer systems and software products connected to medical diagnosis, procedure coding, insurance, and billing systems, and programmed to detect and preempt abuse, fraud, and excessive profits by medical insiders and institutions.

Background

Fraud, in all its forms can be: (a) never caught, (b) caught early, (c) caught late, or (d) prevented altogether. HealthCare fraud has blossomed in recent years because deep pockets like the Government and large insurance companies are now more than ever paying all the bills. That removed the frontline of patients who knew what billings were legitimate and reasonable. The purchasing decisions have been taken away from the purchasers, and they no longer review and approve medical billings. So the new environment makes the rewards of fraud large and the risks of being exposed and punished small.

The once inherent prerogatives of patients to choose doctors, procedures, finance costs, demand explanations, make payments, and even review the totals or get secondary opinions or competitive bids has now been completely requisitioned by the Insurance Companies and Government. As a result, doctors themselves and other first line healthcare providers are incapable of telling patients what the billing costs will be for any of their prescribed drugs or services, there's no reason for them to care or know. All that matters is that "it's covered by your insurance." When told what the costs and consequences are, doctors are often surprised if they're not themselves on the receiving end of those payments.

Insurance Companies and Government, of course, try to control fraud, but their third party, after the fact status to the treatments makes them less able and less effective in controlling medical fraud. Hospitals, clinics, pharmaceutical companies, and other healthcare providers in general have stepped in to capitalize on these shortcomings. Costs, as a direct result have spiraled beyond all reason.

The visibility and insight patients once had fifty years ago acted as a self-limiting and self-correcting mechanism that keep costs low and under control. Patients were uniquely able to negotiate less expensive alternatives in real time, and were motivated to do so because it was they that were paying out of their own pockets.

The computer automation that's starting to take root in the healthcare industry offers some salvation from this disorder. Computer nodes all along the data processing and payment chain can be employed to do cross-checking, sanity tests, behavioral analysis, comprehensive monitoring of single healthcare providers, large database data mining, and even more exotic fraud detection, prevention, and correction.

Medical treatments, procedures, and medicines are expensive and a lot of money flows through the hands that provide them. Some of those hands are not entirely honest or forthright. Others are in the business just to cheat it at every opportunity. The insurance companies and government agencies that process, approve, and payout on medical billings are too distant, too remote, too detached, and too preoccupied to be very good at recognizing when they are being hoodwinked and cheated. Law enforcement is difficult, and crimes related to medical fraud largely go undetected and uncontrolled.

Medicine in America has changed radically from private doctors who did house calls and billed the patients in cash on-the-spot, to anonymous clinics that process thousands of medically insured patients who never see what their doctors or clinics are billing their insurers. These modern patients are completely prevented and disallowed from shopping for treatments and diagnosis, and all the old competition and cross-checking it produced have evaporated. Nothing is left to expose or identify fraud because the billings run open-loop to third parties with no independent methods of verification to rely on.

More and more medicine in America is moving to electronic records, billings, and payments. This then provides an automated means for data to be collected and analyzed. Such collection can occur even before the underlying procedures get paid for by the government agencies or insurance companies. A diagnosis of real-time fraud can be used as an alert to catch the fraudsters red handed and before they get their hands on the money.

CHARLES PIPER identified in a January/February 2013 Article he published in Fraud Magazine:

TEN COMMON HEALTH CARE HEALTHCARE PROVIDER FRAUD SCHEMES

1. Billing for services not rendered.
2. Billing for a non-covered service as a covered service.
3. Misrepresenting dates of service.
4. Misrepresenting locations of service.
5. Misrepresenting healthcare provider of service.
6. Waiving of deductibles and co-payments.
7. Incorrect reporting of diagnoses or procedures (includes unbundling).
8. Overutilization of services.
9. Corruption (kickbacks and bribery).
10. False or unnecessary issuance of prescription drugs.

Conventional defenses to healthcare fraud have had mediocre results, they often waste and abuse space, and have little scalability. Most require high manual effort.

What can be seen, and what fraud and abuse-detection systems report, is never the real problem. A key characteristic of most white-collar fraud and abuse cases is that unless they are detected close to the time they are committed, they will probably remain undetected forever. Certainly the money absconded will never come back. And the way things work in America, only the Government, Lawyers, and Insurance Companies will benefit many years later from any kind of fines, penalties, or restitution that gets imposed in a Consent Order. The patients who were abused will never see any of it.

Fraud and abuse tend to thrive when aggressive prevention procedures are not in place. Healthcare fraud and abuse control is a perpetual, never-ending game, not one that can be won and held. fraud and abuse controls target criminals who distinguish themselves by their great ingenuity. They continuously adjust and adapt their techniques, and blossom on concocting intricate new rip-off schemes.

A static set of "filters" therefore will have only short-term value. Conventional answers and responses to fraud and abuse can never deliver real prevention because they must first be aware of the fraud and abuse before fraud and abuse can be detected, so they are unable to detect new types of fraud and abuse as they occur. Furthermore, they require massive amounts of historical data to recognize patterns and the quality of the system depends on the quality of historical data gathered. All fraud and abuse possibilities must be coded and lack adaptation to new types of fraud and abuse. Therefore, like current virus programs, current fraud and abuse technologies are outdated as soon as they are released. This is clearly inadequate in a world of ever-more clever thieves.

There are critical characteristics of fraud and abuse, such as unpredictability, exponential growth and more sophisticated and advanced fraud and abuse techniques, that, when addressed by the proper technology, can be successfully curtailed. However, current systems employ methods that do not respond to these changes.

Computer scientists initially created programs called fraud and abuse Scanners that detected known cases of fraud and abuse by using a profile or signature that uniquely identified these instances of fraud and abuse. These signatures were cataloged and stored in a database as part of the anti-fraud and abuse program. For each transaction, the anti-fraud and abuse program scanned and compared them to the known signatures stored in the database. If a match occurred, the file was determined to be fraudulent.

This method, called Known-fraud and abuse Scanning, proved useful during the first few years of the fraud and abuse scourge, but today it is completely ineffective. The problem is that keeping the database current requires updating the database as soon as new fraudulent activity is discovered.

With new fraud and abuse appearing each new day, company employees would have to update their computer's anti-fraud and abuse databases just as often (and only in the event that they receive a warning about it before it costs their company).

The best of the conventional fraud and abuse detection systems still use Neural Network back propagation (BP) algorithms. BP Neural Networks learn the patterns in the relationships between inputs and outputs, and then are able to respond intelligently to new inputs, e.g., using the experiences gained during training. BP networks belong to a supervised-learning class of Neural Networks. The error signals they produce during training are used to supervise the learning process. Neural Networks that use supervised learning techniques have proven themselves in classification, generalization and prediction and many other practical applications. But, needing to know what output is desired for each input before any training begins can be very limiting.

When the desired outputs are unknown during training for less than all input patterns, new incidences of fraud and abuse may not be detected in real-time. There is a crucial lag between detection and infection (fraud and abuse arrival).

Neural Networks, statistical modeling or profiling have been applied to fraud and abuse detection. But for them to be effective, they need a large database of cases in which fraud and abuse were detected. However, for this to work later the fraudulent methods and abuse must not have changed much. Such tools are impotent when the fraud and abuse either too closely resembles normal activity, or if it constantly shifts as the fraudsters adapt to changing surveillance strategies and technologies. (Which, by the way, is what the influenza virus does naturally.)

In Intelligent Fraud prevention the "leakage" in the industry is the problem. Illegal activity, while significant in absolute numbers, is trivial when compared to a $2.8 trillion in annual healthcare spending. The solutions provided must address the breadth of the leakage. For example, simple excessive billing of preventive visits (Evaluation and Management claims) results in $20-$30 inflated billing per visit. With one billion primary care physician visits each year, that leakage alone exceeds the entire fraud recoveries in the industry in a single year.

Conventional analytic solutions, even those that claim to be non-hypothesis based, still operate within very rigid boundaries. They are either designed or tuned to look at various scenarios in such a way that they will only catch a limited range of the leakage problem. When something truly surprising happens, or a variation occurs that was not anticipated, systems based on such models fail to perform.

Modern systems need to be sophisticated, unsupervised, learn as they go, and conduct peer reviews based treatment, zip code, etc.

Conventional fraud and abuse detection systems are like Virus Tools, they must be instructed and supplied with templates to detect fraud and abuse. These the expense of pioneers who were hit first and early. This is clearly laughable in a world of ever-more clever thieves.

New behaviors of fraud and abuse arise daily.

Conventional solutions to healthcare fraud, waste and abuse space have obtained only mediocre results. They lack scalability and always require high manual effort. We can do better.

SUMMARY OF THE INVENTION

Briefly, real-time fraud prevention embodiments of the present invention comprise a software-as-a-service (SaaS) product with computer instruction sets to enable a network server to receive medical histories, enrollments, diagnosis, prescription, treatment, follow up, billings, and other data as they occur. The SaaS includes software instruction sets to combine, correlate, categorize, track, normalize, and compare the data sorted by patient, healthcare provider, institution, seasonal, and regional norms. Fraud reveals itself in the ways data points deviate from norms in nonsensical or inexplicable conduct. The individual behaviors of each healthcare provider are independently monitored, characterized, and followed by self-spawning smart agents that can adapt as the healthcare providers evolve. Such smart agents will issue flags when their particular surveillance target is acting out of character, outside normal parameters for them. Fraud controls can therefore be much tighter than those that have to accommodate those of a diverse group.

The above and still further objects, features, and advantages of the present invention will become apparent upon consideration of the following detailed description of specific embodiments thereof, especially when taken in conjunction with the accompanying drawings.

BRIEF DESCRIPTION OF THE DRAWINGS

FIGS. 3A-3C are diagrams representing the use of historical claim data during training to build predictive models, the running of sample claim data to discover clusters and group behaviors, and the processing thereafter of real-time claim data to detect fraud;

DETAILED DESCRIPTION OF THE INVENTION

In general, healthcare fraud prevention embodiments of the present invention automatically spawn and assign "smart agents" to follow and develop behavioral dossiers for corresponding individual health care healthcare providers. The embodiments are implemented as a software-as-a-service (SaaS) that is hosted by or in cooperation with a medical payments processor. As many as ten MINDSUITE™ classification modeling technologies are organized to compute their individual scorings and send their results to the smart agents. Each employs their own particular analytical panache to classify the claims as they arrive.

The smart agents are empowered to give weight or ignore inputs from each of the classification models according to their own assessments. Real-time, long term and recursive profiling is used to help identify what is normal in a multi-dimensional space for the behavior of the health care healthcare provider corresponding to the claim data. See, "A Roadmap of Agent Research and Development", by Nicholas R. Jennings, et al., Autonomous Agents and Multi-Agent Systems, 1, 7-38 (1998), (c) 1998 Kluwer Academic Publishers, Boston. Manufactured in The Netherlands.

Figure 1:
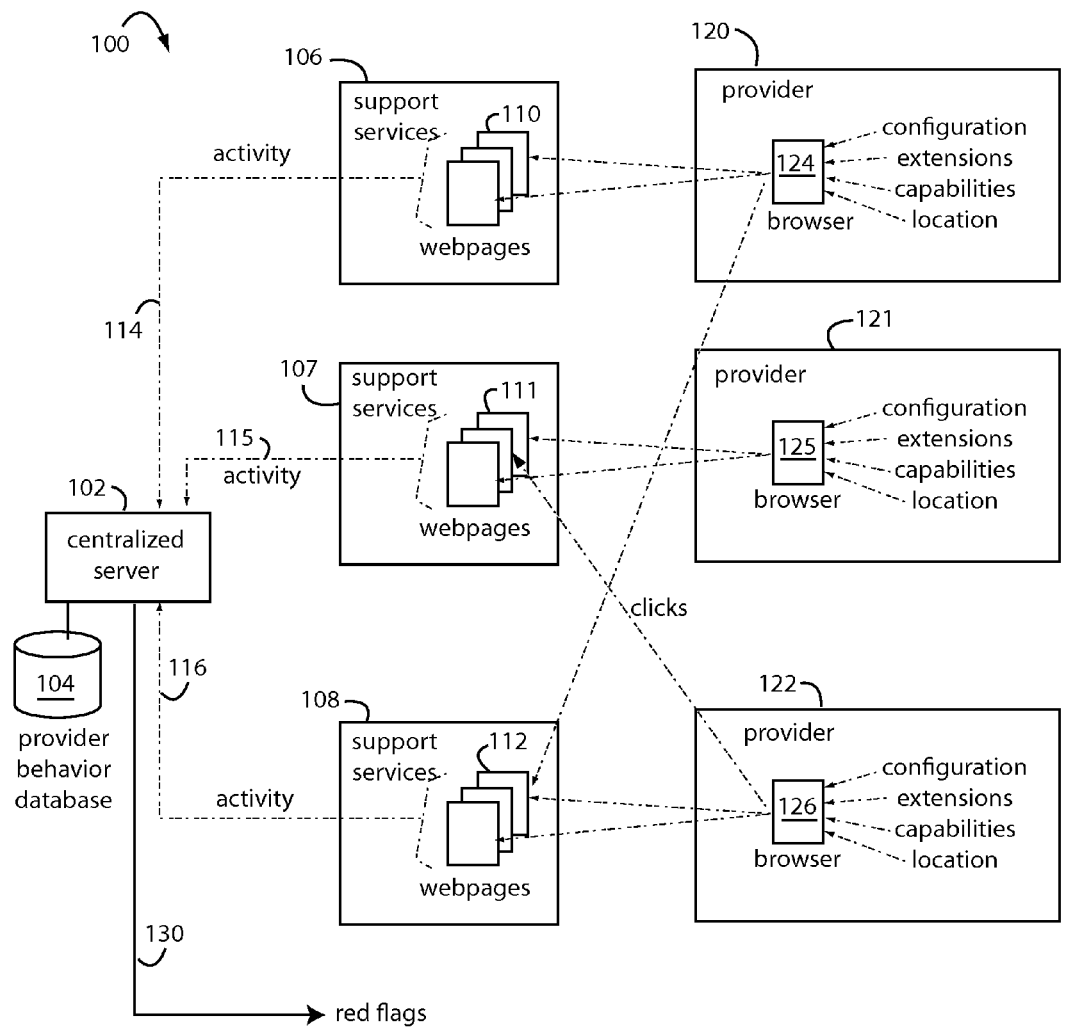
FIG. 1 is functional block diagram of a network-based system embodiment of the present invention for controlling fraud in the health care industry. The three websites shown represent what can be millions of independent websites on the Internet, and the three healthcare industry healthcare providers represent millions of unrelated and independent healthcare industry healthcare providers of all types.

FIG. 1 represents a network-based system 100 for controlling fraud in one corner of the health care industry. System 100 is anchored by a centralized server 102 with a healthcare provider database 104. These support several independent, secure, and private medical websites 106-108, each supporting data reporting webpages 110-112. Each such website 106-108 sends healthcare provider activity reports 114-116 to the centralized server 102 in real-time over the network.

What could be thousands, or even millions of healthcare industry healthcare providers, are represented here in FIG. 1 as healthcare industry healthcare providers 120-122, each has a browser or app 124-126 capable of surfing or visiting support services webpages 110-112. Each healthcare industry healthcare provider 120-122 can freely access any support services website 106-108, but when they do, their patient data and healthcare provider behaviors become the subject of activity reports 114-116. The healthcare industry healthcare providers themselves use the spectrum of mobile smartphones, tablets, laptops, and desktop computers to access accounts and submit payment claims.

The browsers and apps 124-126 associated with this spectrum vary tremendously, as do their particular configurations, extensions, capabilities, and locations, not to mention a hundred other parameters and characteristics. Each healthcare industry healthcare provider will usually be associated, at least temporarily, with a unique Internet IP address that can reveal the geographic location of the healthcare industry healthcare provider.

Many of these configurations, extensions, capabilities, locations, and other parameters and characteristics are volunteered by or can be queried from browsers and apps 124-126 and collected by websites 106-108.

The goal of system 100 is to report and issue scores and flags 130 that call out particular healthcare providers and detail the suspicious behavior for auditors and law enforcement to act on. A minimum of false positives and false negatives are critical to any commercial viable product.

Figure 2:
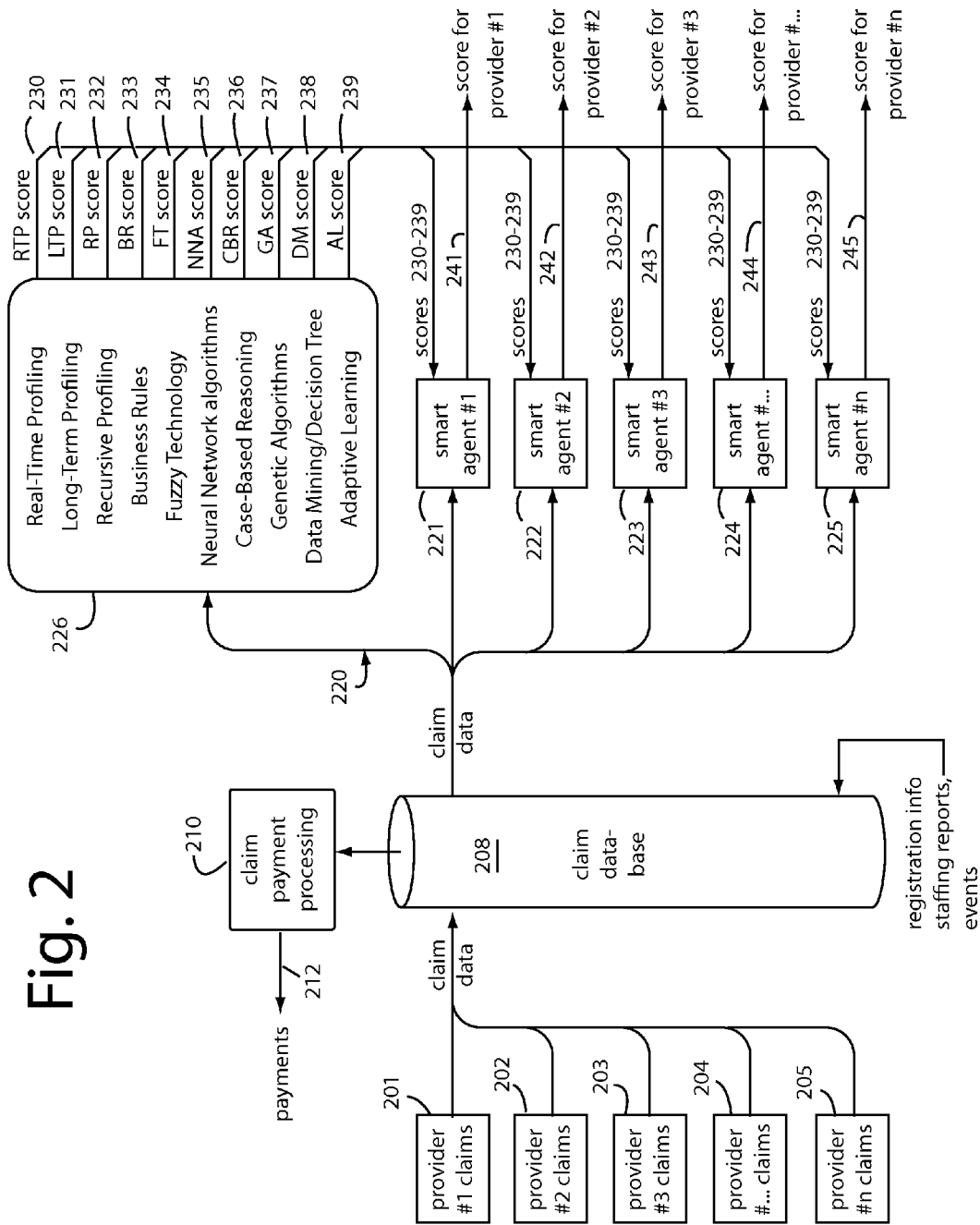
FIG. 2 is a function block diagram of a computer network collecting medical claims from health care healthcare providers, processing payments, and a fraud assessment and detection scheme useful in the system of FIG. 1.

FIG. 2 will illustrate a practical approach. Classification is a form of data analysis used by embodiments of the present invention for fraud detection. Ideally, healthcare provider claims will ultimately classify into legitimate and fraudulent, with zero false positives and zero false negatives. More often, some items will classify as questionable needing further investigation, and what exactly triggered a false positive or a false negative can wander and vary. Fraud itself adapts to changing environments and embodiments of the present invention are self-learning, adaptive, and responsive in real-time.

Data classification model building begins with a learning step, and is followed by a test of the performance. In the first step, a mapping function $y=f(x)$ is learned that can predict the associated class label y of a given tuple x. Once trained and tested, the variables reported in the claim data in each reporting category are fit to a tuple. The mapping function can be in the form of classification rules, decision trees, or mathematical formulae.

A decision tree has internal nodes that each represent a different test on an attribute, and each branch represents an outcome for the preceding test. Each leaf node holds a class label. Attribute selections are used during tree construction to find those attributes that best partition the tuples into distinct classes.

Once a decision tree has been built, tree pruning is used to identify and remove branches that sprouted during learning from outliers and plain noise in the training data. Once trained, decision trees can then be employed to classify the claim data inputs. For each tuple x in which the associated class label is unknown, the attribute values of the tuple are run through the decision tree. Paths will trace through from the root to a leaf node, and that represents a prediction of the tuple's class. Decision trees directly convertible into classification rules.

Rule based classifiers use IF-THEN conditional constructions for classification. The IF condition is the logical AND of the attributes that produced the leaf in the decision tree. The outcome is the class prediction.

Back propagation is a type of learning algorithm in a neural network with a set of interconnected units. Each input connection has a weight associated with it. The best weights to assign each input are determined during a learning phase. Those weights that best predict the correct class label of the input tuples are adopted. Back propagation performs well in multilayer feed-forward neural networks.

Genetic algorithms represent one of the best ways to solve for unrecognized problems, and will work well in any search space. All you need to know is what you need the solution to be able to do well, and a genetic algorithm will be able to create a high quality solution. Genetic algorithms iteratively select and evolve inputs and weights to find solutions to problems. Genetic algorithms do well in environments with large sets of candidate solutions, and in which the search space is not even. Specific algorithms in simpler search spaces do better.

Genetic algorithms can take quite a while to run. They are, however, one of the most powerful methods for finding high quality solutions to problems.

FIG. 2 represents a health care fraud prevention software-as-a-service (SaaS) 200 that receives medical payment claims by thousands, or even millions of healthcare industry healthcare providers and healthcare providers, represented here in FIG. 2 as healthcare providers respectively submitting healthcare provider claims (1:n) 201-205. SaaS solutions are a "Cloud" implementation of a network of specialized servers that can be secured and have its costs amortized across millions of users.

The healthcare provider claims are collected into a large relational database 208. Experience tells us that some percentage of these healthcare providers can be expected to submit fraudulent healthcare provider claims (1:n) 201-205. Such Claims will appear legitimate on brief review, and can dupe a claim payment processor 210 into issuing payments 212 in excess of what the Law or the healthcare providers' contracts allow.

Collected and job scheduled claim data 220 is fetched from the relational database 208 and forwarded to corresponding smart agents (1:n) 221-225. Each smart agent is assisted and signaled by case-by-case analyses provided in real time by several classification models or technologies operating in parallel that independently "crunch" the claim data 200 according to their own styles and methods. These are combined here for illustration in an analytical engine 226 for testing with a suite of classification models.

Smart agents can have relationships to other smart agents that may be important to the detection and reporting of healthcare claim fraud. For example, given healthcare providers A-F, the corresponding smart agents for healthcare providers A and B will have a mutual relationship of locality if they are in the same area. Healthcare providers C and D will have a mutual relationship of co-workers if they are employed by the same employer. Healthcare providers E and F will have a relationship of referral if one refers patients to the other. Relationships are a basis for clustering. Clusters that express higher levels of fraud may be doing so because of the underlying relationships. Or vice versa, the underlying relationship may explain satisfactorily why the cluster has non-normal behavioral facets.

A conventional relational database system can be usefully employed to implement millions of smart agents with complex inter-relationships that change over time. Program daemons can be assigned to keep the smart agents attended to in real-time.

Other useful technologies include computer modeling processes for: business rules, fuzzy technology, neural network algorithms, case-based reasoning, genetic algorithms, data mining, adaptive learning, etc. Each process is capable of independently outputting a corresponding score 230-239 when it determines abnormal behavior.

The smart agents are self-learning and adaptive, they each build on the claims experiences they have with the healthcare providers they follow. We illustrate and describe them herein in a variety of ways and from a number of perspectives to show how useful and novel smart agents are in the ways we employ them. Real-time profiling, long-term profiling, recursive profiling are used in new situations the other classification models would miss, or misinterpret by getting out-of-date.

Conventional classification models are limited to using what is immediately before them in the claim data and applying to that rules and structures that are inflexible. Profiling recognizes that normal behavior does not always appear normal in every sample. So in instances where scores from the classification models 226 cannot agree, the smart agents will use the profiling they maintain internally on the corresponding healthcare provider to assign a final classification of good/maybe/bad to the claim.

Smart agents all start out constructed the same, a bare bones profile with a standard inventory of empty behavioral facets. Smart agents are spawned as needed or put to sleep as appropriate in order to always be able to accommodate and follow every active healthcare provider over time. Each smart agent (1:n) 221-225 learns its corresponding healthcare provider's individual behaviors in a variety of situations, diagnoses, patients, treatments, claims, and follow-ups. What each smart agent retains as normal behavior tallies in each aspect and facet for its corresponding healthcare provider can diverge as a whole from the others as more experience and familiarity with their surveillance targets are collected. This occurs rapidly when initializing with supervised data.

In contrast, conventional detection engines like in Artificial Neural Networks (ANNs) are tuned by Genetic Algorithms (GA's) that can determine 1) an optimum set of input factors for the ANN, 2) the optimum topology for the ANN, and 3) the optimum weights for the ANN neurons.

ANN models are based on biological neural networks, and consists of interconnected groups of artificial neurons that compute information according to how they are connected. ANN's change their structure based on the information flowing through the network during a learning phase. ANN's can model complex relationships between inputs and outputs and find patterns in data if they exist. Searches with genetic algorithm (GA) global search heuristics can find exact or approximate solutions to optimization and search problems. Genetic algorithms use inheritance, mutation, selection, crossover, and recombination techniques.

Analytical engine 226 includes real-time profilers that analyze the data as they come in, and use it to update aspects of each profile. Flags can issue or fraud scores 230 can raise if something appears out of character.

The long-term profilers in analytical engine 226 draw conclusions and assumptions from a healthcare provider's behavior as it has been collected over several different spans of time, e.g., months or even years. Scores 231 can issue if the present behavior is out of character with long term behaviors.

Recursive profilers are included that follow the customers that regularly visit the facilities. They can self-adapt to behavior changes as they occur with each healthcare provider. Individual adaptations allow tighter bounds to be used. These are more likely to trigger the output of a real-time profile score 232 when some aspect of a claim seems out-of-bounds of business rules, for example.

Analytical engine 226 includes business rule checkers to test for activities that fall outside business norms or that are in violation of the business' policies, or that experts have concluded are telltale of problems. This then implies the business rules are defined in the programming, and a mapping to them is provided for relevant claim data inputs. A business rule score 233 will issue if a business rule violation seems to be inherent in claim data 220.

Fuzzy logic can provide a "maybe" to the question of fraudulent claim reporting when other classification models are limited to a more definite yes or no. A fuzzy logic score 234 will help the corresponding smart agent to make a final decision in order to reduce false positives and false negatives.

Analytical engine 226 includes the use of neural networks that interpret historical data to identify trends and patterns against which to compare subject cases. Neural networks here translate a database into neurons without user intervention, and will significantly accelerate the speed of convergence over conventional back propagation, and other neural network algorithms. The present invention's neural net is incremental and adaptive, allowing the size of the output classes to change dynamically.

Neural networks can detect trends and patterns other computer techniques are unable to. An Artificial Neural Network, (or an ANN), is an information-processing paradigm that models the way in which biological nervous systems, like the brain, process information. Most known neural networks have at least two layers, 1) input layers relate to what the smart agent receives from the environment, and 2) output layers, which correspond to the smart agent's potential actions. Back Propagation and others use one or more intermediate layers between these two layers. These layers are highly interconnected, as the units on one layer are connected to those in the next layer. The factors that shape a neural network are its environment and its genetic makeup. Both its initial state and its training play a role in the ANN's development.

It is through the critical training process that ANN's are taught how to arrive at the correct answer. This training process works much in the same way that a child comes to learn, for example, not to eat a particular food that repeatedly causes an upset stomach. Through different samples and experiences, the child eventually stops eating this food. So clearly, a well-trained neural network will be more successful than a poorly trained neural network (the training referring to its environment and the experiences and samples that help shape it). The more samples (experiences) to which a neural network has a direct correlation, the greater the likelihood of its success.

A neural network problem exists when there is no effective algorithm or IF-THEN rules that can be used to solve it. Neural networks are ineffective when exact rules cannot be specified and when human judgment is required. Once the problem identified, a choice can be determined from an array of neural networks each with different virtues. Back Propagation, for example, is a good mapping network.

Case-based reasoning (CBR) processes included in analytical engine 226 use past experiences to help solve current problems. Case-based systems search their case memories for a pre-existing case that matches the current input specifications. As new cases are solved they are added and continue to increase the database of cases solved. Thus continuing to increase the likelihood of success.

The goal of CBR is to find a case that matches the input problem, to then go directly to an already successful solution. Making it possible to provide solutions to potentially complex problems quickly. If, on the other hand, an exact match cannot be found, the CBR system may find one similar to the present input, and present it as a possible solution. Since CBR systems can learn, whenever a non-perfect match is found but the problem is nevertheless solved, the case parameters are added to the case memory for future reference. Learning is thus a key part of a CBR system's architecture. A CBR score 236 will issue if previous instances have discovered fraud with the present input variables.

Genetic algorithms (GA's) are optimization techniques that are used herein to identify what seems to be the most important fields in a data layout. They can spot important individuals operating in a large, otherwise homogeneous population. Genetic algorithms evaluate models they create using random fields and selections. Then generation-by-generation more optimal choices are discovered to design the predictive models. Genetic algorithms are evolutionary algorithms in which the aim is to obtain better and seemingly optimal solutions. Genetic algorithms can be used to comb through large and undefined search spaces. A problem here will output a GA score 237.

Analytical engine 226 uses data mining methods to extract implicit, previously unknown and potentially useful information from claims database 208. E.g., to distill a Decision Tree. The data mining searches for relationships and patterns that may be hidden in the claim data. Particular classifications, association rules and analyzing sequences are used to extract data. It is then analyzed and can be presented graphically. Many different technical approaches are used to address data cleaning, sampling, automatic enrichment of the data by automatically creating new fields based on aggregation, time-window, velocity, etc.; and also clustering, learning classification rules, analyzing changes and detecting anomalies. Such data mining can sometimes help to automatically generate business rules from the claim data.

Adaptive learning combines three learning techniques, the automatic creation of profiles (smart-agents) from historical data (long-term profiling), the enrichment of smart-agents based on real-time activities, and adaptive learning carried by incremental learning algorithms.

As a start, two years of credit card transaction historical data over twenty-seven terabytes in size was obtained from a database. Smart-agents for each individual payment card with long-term profiles were built in a first pass. Each profile gets created with all the learning obtained from the card activities and transactions over the two years period.

Behaviors are manifested in many aspects. Each smart-agent profile maintains facets that are each running extracts of these manifestations. Smart agents for tracking credit card behavior typically include merchant category code (MCC), time, amount for an MCC over a period of time, recursive profiling (zip codes), type of merchant, monthly aggregation, activity during the week, weekend, holidays, card-not-present (CNP) versus card-present (CP), domestic versus cross-border, etc. A properly defined profile can track all the important activities for a specific payment card.

Data mining technology is used to create credit card fraud detection decision trees from transaction data histories. But data mining can only learn from historical data, it generates single decision trees that must apply broadly to the group of cardholders in the historical data. Such leads to poor fit because the one decision tree has to apply the same logic to all the cardholders. Merchants, like Target, can have unique activity patterns, and each cardholder too can have unique spending patterns.

Another limit to data mining is the decision trees can be outdated as soon as they're put to use, fraud schemes change. If the decision trees are not constantly updated with examples of the new types of fraud schemes, the decision trees will fail. The ability to adapt to new fraud schemes is critical due to the highly volatile nature of fraud.

Another technology widely used is Business Rules which require experts to write IF-THEN-else logic rules. There are limits to this technology as well. Business rules require rules to be written that will work for whole categories of customers. This requires the population to be sliced into many categories, e.g., students, seniors, zip codes, etc. The experts then must devise rules that can be applied to all the cardholders of a category.

For example, trying to slice the US population into categories would not succeed. All the cardholders in a category would not necessarily have the same behavior. Businesses have many limits with poor detection rates high false positives. It is also obvious that such rules will get out-of-date as soon as they are written. They are not engineered to adapt as new fraud schemes and data shift with time.

Neural network technology also has its limits, historical data is used to create matrix weights for future classifications. Neural networks will use historical transactions as input (first layer) classifications for fraud. Neural Networks only learn from past transactions, and cannot detect new fraud schemes that arise daily.

Classification logic learned from historical data decision trees is immediately outdated because the fraud schemes can change.

Smart-agent technologies learn from the specific behavior of each cardholder, they create a smart-agent to follow the behavior of each cardholder. Each cardholder activity provides a lesson, the smart-agents update profiles and make changes effective at runtime. As such, smart-agents is the only technology that can identify and stop previously unknown fraud schemes in real-time.

Smart-agent technologies have the highest detection rates with the lowest false positives because they each learn the behavior and follow separate cardholders.

Conventional technologies that needed to store and use twenty-seven terabytes of historical data to follow 27-million cardholders, now contrasts with smart-agents using profiles needing only two hundred gigabytes of storage. Thus, for example, a data reduction step may be carried out for converting claim profile data comprising a plurality of behavioral dimensions, wherein a minimum of a hundred fold reduction in data volume may be realized.

Adaptive learning can embed incremental learning technologies in conventional machine learning algorithms. As smart-agents learn from false positives and negatives, each corresponding classification technology is amended with automatic updates.

For example, the data mining classifier incrementally changes the decision trees by creating new links or updating existing links and weights. Neural networks update their weight matrices. Case-based reasoning classifiers have their generic cases updated or new ones are created.

Smart-agents update profiles, in general, by adjusting the normal/abnormal values linked to the profile, or by creating new exceptions.

Returning to FIG. 2, smart agents 221-225 can teach themselves how much weight to give each score 230-239 based its experience with the healthcare provider's behavior. Some scores 230-239 can be very important with particular healthcare providers, and yet with others they can be unimportant and dismissed.

If however, any smart agent 221-225 judges claim data 220 to be suspicious in the context of its corresponding healthcare provider, then a score 241-245 will issue identifying the healthcare provider and details on why their claim is suspicious. It then is for the business auditors and/or law enforcement to intervene, assess, decide, and act to stop the fraud.

Smart agent 221-225 track the multi-dimensional behavior of individual healthcare providers and aggregate data in each dimension. The data collected and accumulated in order to build Profiles is provided in each dimension by sampling the medical claim data each healthcare provider presents for payment. Some samples may require related or associated records to be input that must be tied together, e.g., what service was provided by code, who provided it, where it was provided, and what follow up occurred. These are cross correlated with site rosters, work schedules, and follow ups expected by initial coding.

It could be arbitrarily established that any new claim data 220 coming in for a particular behavioral dimension that is within ±1 sigma of average will be classified as high confidence of normal, non-fraudulent behavior. New claim data 220 coming in for a particular behavioral dimension outside that but still within ±2 sigma of average will be of marginal confidence of normal, non-fraudulent behavior and needs further analysis and input, e.g., scores 230-239 from analytical engine 226.

It could be established by a business rule, and managed by analytical engine 226, that any new claim data 220 coming in for a particular behavioral dimension outside ±2 sigma of average signals fraudulent behavior and needs attention by auditors or law enforcement.

Group smart agents are also spawned to provide benchmarks for clusters or groups of healthcare providers sending in claim data 220 with differing medical specialties, geographical distributions, organizations, etc. An individual smart agent 221-225 may not trigger a score 241-245 on the behavior of its surveillance target healthcare provider, because their behavior is running normal for them, but when compared to the multi-dimensional group behaviors of their peers there appears to be a deviance from conventional practice. Or vice versa.

The individual healthcare provider behaviors that have been of traditional concern to managers and Government administrators is summarized in the following Table, Behavior Targets. Smart agent embodiments of the present invention that are directed to healthcare fraud detection would therefore need to include standardized sets of aspects and facets in the profiles they maintain that preserve indicia of target behaviors.

Behavior Targets

1. Reporting diagnoses or procedures using "up-codes" to inflate billings.
2. Billing for services not actually furnished.
3. Billing that appears to be a deliberate application for duplicate payment for the same services or supplies.
4. Misrepresenting the dates and descriptions of services furnished or of the identity of the beneficiary.
5. Billing for non-covered or non-chargeable services as covered items.
6. Incorrect cost distributions on cost reports.

| Behavior Targets |
| --- |

7. Including costs of non-covered services, supplies, or equipment in allowable costs.
8. Arrangements between healthcare providers and employees, independent contractors, suppliers, and others that appear to be designed primarily to overcharge the program through various suppliers to siphon-off and conceal illegal profits.
9. Billing Medicare for costs not incurred or which were attributable to non-program activities, other enterprises, or personal expenses.
10. Repeatedly including unallowable cost items on a healthcare provider's cost report except for purposes of establishing a basis for appeal.
11. Manipulating statistics to obtain additional payment, such as increasing the square footage in the outpatient areas for maximizing payment.
12. Claiming bad debts without first genuinely attempting to collect payment.
13. Certain hospital-based physician arrangements and amounts actually paid to physicians.
14. Amounts paid to owners or administrators that have been determined to be excessive in prior cost report settlements.
15. Days that have been improperly reported and would result in an overpayment if not adjusted.
16. Depreciation methods not approved by Medicare.
17. Interests expense for loans that have been repaid for an offset of interest income against the interest expense.
18. Program data where healthcare provider program amounts cannot be supported..
19. Improper allocation of costs to related organizations that have been determined to be improper.
20. Billing for services or supplies that were not provided.
21. Altering claim forms to obtain a higher payment amount.
22. Billing twice for the same service or item.
23. Billing separately for services that should be included in a single service fee.
24. Misrepresenting the diagnosis to justify payment.
25. Continuing to bill for services or items no longer medically necessary.
26. Billing for rental equipment after their date of return.
27. Billing "non-covered" services or items as "covered" services.
28. Ordering unnecessary lab tests.
29. Using another person's Medicare card to obtain medical care.
30. Completing a Certificate of Medical Necessity (CMN) for a patient not professionally known by the healthcare provider.
31. Completing a CMN when not authorized (for example, a supplier completing a CMN for the physician).
32. Signing authorizations for medical equipment or procedures that are not medically necessary.
33. Waiving co-insurance or deductibles.
34. Billing for home health care services for patients who do not meet the requirement of "homebound" status.
35. Using unethical or unfair marketing strategies, such as offering beneficiaries free groceries or transportation to switch healthcare providers.
36. Billing for social activities and calling it psychotherapy.
37. Billing group services as individual services for each patient in the group.
38. Repeatedly violating the participation agreement, assignment agreement, or limiting charge.
39. Outpatient hospital services provided within 72 hours of surgery or other inpatient.
40. Inflating the number of days the patient staid in hospital.
41. Discharging and then immediately readmitting to same hospital.
42. Payments for related hospital and skilled nursing stays.
43. Skilled nursing coverage after unnecessary hospital stays.
44. Prospective payment system transfers.
45. Between chain members.
46. Uncollected beneficiary deductibles and coinsurance.
47. Diagnosis-related group analysis.
48. Outlier payments for expanded services.
49. Changes in the inpatient case mix index for Medicare.
50. Diagnosis-related group payment window.
51. Outpatient hospital psychiatric claims.
52. Outpatient hospital revenue centers without common procedure codes.
53. Mental health reviews.
54. Treatment plan issues
55. Home Health analysis.
56. Peer review comparison.
57. Nursing Home Resident Assessments.
58. Nursing Home Vaccination Rates: State Initiatives.
59. Physician Routine Nursing Home Visits.
60. Therapy Services in Skilled Nursing Facilities.
61. Durable Medical Equipment Carriers.
62. Duplicate Billings for Medical Equipment and Supplies.
63. Appropriateness of Home Medical Equipment and Supplies.

| Behavior Targets |
| --- |
| 64. Medical Appropriateness of Tests and Other Services.
65. Questionable Claims.
66. Medicare Outpatient Prescription Drugs.
67. Medicare Payments for "Not Otherwise Classified
68. Outpatient Rehabilitation Facilities.
69. Comprehensive Outpatient Rehabilitation Facilities.
70. Vulnerable Medicare Beneficiaries.
71. Clinical Laboratory Proficiency Testing.
72. Excess Payments for Ambulance Services.
73. General and Administrative Costs.
74. UP CODING
75. Emergency Services to Enrollees of Medicaid Managed Care
76. Hospital-Specific Disproportionate Share Payment Limits.
77. Payments for Services to Dually Eligible Beneficiaries.
78. Medicaid Payments to Institutions for the Mentally Retarded.
79. Medicaid Outpatient Prescription Drug Pricing.
80. Billing for Resident Services. |

The medical claim data 220 received and other information on file or that can be queried can reveal if any of the above Target Behaviors are present by a process of "connecting-the-dots". For example, if a healthcare provider routinely sees twenty patients per hour all day, but then sees two hundred per hour, then those claims might be fraudulent. One dimension in the smart agent used to track the number of patients seen per hour of the day will automatically trigger the abnormality versus what it sees normally. The raw medical claim data 220 would have to be mined for this by sorting according to time and place of services delivery. Patients seen after hours, or on weekends, holidays, or vacations, all too raise concerns of fraud. But, seeing patients off hours may be normal behavior for some healthcare providers, in some locations, or in connection with unusual local events. These other factors are then important to track as behavioral dimensions. A smart agent could learn these variations or excursions in behaviors are normal.

More than simple claim data 220 will be required in order to "connect-the-dots". While each instance of claim data 220 has its healthcare provider fully identified, many important details necessary needed to make inferences and other extrapolations will only come when also given data from healthcare provider registration and licensing forms, work schedules, facility lists, etc. These data can be held in data base 208 and related to each healthcare provider reporting.

Mixed smart-smart agent technology embodiments of the present invention have the novel ability to recognize unknown and new types of fraud and abuse. They do it with real-time profiling, long-term profiling, recursive profiling, and adaptive learning.

Just about all fraudulent and abusive activities tend to exhibit at least some abnormal behaviors. So watching for these behaviors can simplify the job of fraud prevention and will never go out-of-date.

Abnormal and inconsistent behaviors are flags for fraud and abuse. A computer can be programmed to collect and profile various facets and aspects of the behavior of healthcare providers. The resulting behavioral profiles can be usefully employed to anticipate, adapt, and predict even never before seen frauds.

FIGS. 3A-3C represent the three run-times that follow compile-time system construction as a software-as-a-service (SaaS) healthcare fraud supervisory system product 300. In FIG. 3A, historical claim data 302 that includes training data is run through during supervised learning, but not maintained within SaaS 300. This builds predictive models 304 within analytical engine 226 (FIG. 2), e.g., case-base studies, decision trees, food for data mining, weightings, etc. The respective smart agents are loaded with long-term profile data for specific healthcare providers over their individual histories.

FIG. 3B represents an "unsupervised learning" session for SaaS 300 in which sample claim data 306 is run through so that clusters of healthcare providers and their group behaviors can be identified to create groupings and categories. These can help reduce false positives and false negatives when an individual healthcare provider appears to have strayed in some facet.

"Clustering" will identify groups in the claim data that can be collected into clusters 308 of objects having similar components to them. The data as a whole can be modeled by these clusters, with only a small loss of the fine details. The simplification achieved is worthwhile. The individual member smart agents continue to live on and operate independently.

The identification of clusters is akin to recognizing hidden patterns in the claim data. Cluster searches through sample claims 306 are opportunities for unsupervised learning. Clustering in data mining applications has deep roots in scientific data exploration, information retrieval and text mining, spatial database applications, Web analysis, customer relationship management, marketing, medical diagnostics, computational biology, etc. Any of a number of conventional clustering algorithms can be used in FIG. 3B. See, "Survey of Clustering Data Mining Techniques", by Pavel Berkhin, Accrue Software, Inc. (San Jose, Calif.)

| CONVENTIONAL CLUSTERING ALGORITHMS |
| --- |
| Hierarchical Methods
    -Agglomerative Algorithms
    -Divisive Algorithms
Partitioning Methods
    -Relocation Algorithms
    -Probabilistic Clustering
    -K-medoids Methods
    -K-means Methods
    -Density-Based Algorithms
        --Density-Based Connectivity Clustering
        --Density Functions Clustering
Grid-Based Methods
Methods Based on Co-Occurrence of Categorical Data
Constraint-Based Clustering |

| CONVENTIONAL CLUSTERING ALGORITHMS |
| --- |
| Clustering Algorithms Used in Machine Learning<br>   -Gradient Descent and Artificial Neural Networks<br>   -Evolutionary Methods<br>Scalable Clustering Algorithms<br>Algorithms For High Dimensional Data<br>   -Subspace Clustering<br>   -Projection Techniques<br>   -Co-Clustering Techniques |

FIG. 3C represents a SaaS 300 that has internalized predictive models 304 and ID clusters and categories 308 and is ready to run real-time claim data 310. The output will be high detection rate/low false positive rate fraud classifications 312.

Figure 4:
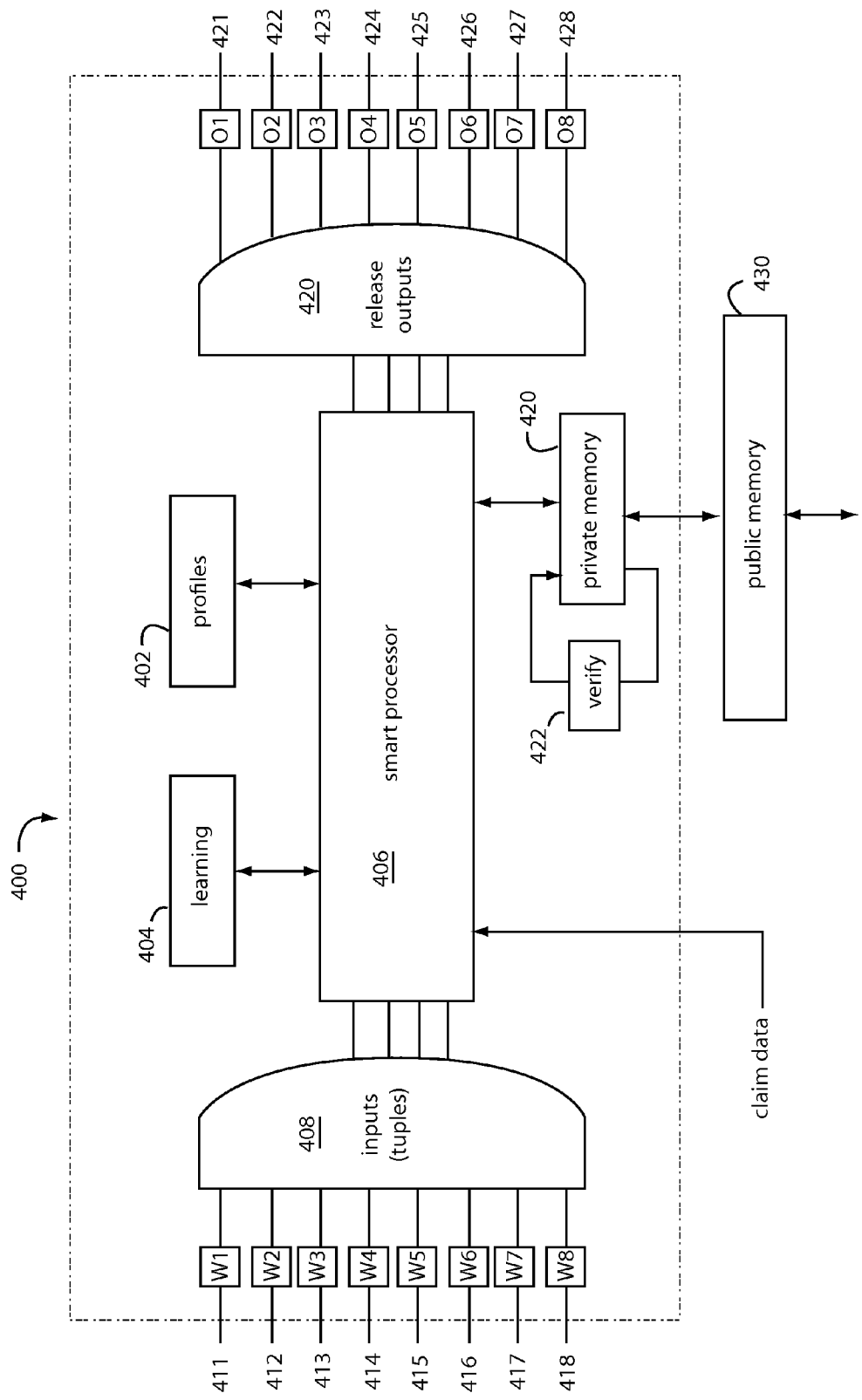
FIG. 4 is a functional block diagram of a smart agent manifested in hardware in order to explain its construction and function. Smart agents are best, in fact, compiled as C++ code using specialized compilers and development systems that produce software-as-a-service (SaaS) computer program files.

FIG. 4 represents a smart agent 400 in an abstract hardware embodiment. Smart agents 400 can be better built of software running on general purpose computers because of the run-time flexibilities that are made possible. But describing the hardware here is done in order to have this explanation go smoother. Smart agents 400, in general will be the machine-code product of a high level language software compiler and other development tools, and may even be invoked whole as a library. In the healthcare fraud embodiments described herein, it is important to have spawned a smart agent 400 to track, monitor, and observe each particular health care healthcare provider capable of fraud.

As new healthcare providers come on the scene during run-time, a new smart agent 400 is automatically spawned and instantly assigned to them. As the new healthcare providers submit their first claims, their initial appearances must be recognized immediately and the new smart agent brought up to speed. The thousands of smart agents 400 spawned during compile-time of the whole system help get things up and running initially.

Each smart agent 400 will have goals 402, e.g., to improve healthcare claim fraud detection and reduce false positives. It gets better at doing this as it gains experience and sees the results of its decisions build up in a knowledge memory 404. Such may be preloaded with general lessons others have learned in order to get a head start. A smart processor 406 reads data in from an input selector 408 and can treat them as tuples. Each input line 411-418 is given a weight W1-W8 that is adjusted according to experiences learned and stored in knowledge memory 404.

When implemented as software, smart agent 400 can be equipped with thousands of inputs that can scale dynamically to far fewer or much more. The hardware implementation shown here in FIG. 4 would not be anywhere near as flexible, and unable to scale in run-time. Each input 411-418 could simply be an address in memory space shared by as many smart agents 400 that need to have that particular input.

A private memory 420 is used to store statistical claim request information related to a particular doctor, hospital, equipment healthcare provider, drug supplier, outpatient facility, long term care facility, etc., or groups of them. Beneficiary-specific, healthcare provider-specific, doctor-specific data is needed to be able to sort the claims and to spot any correlations.

The data stored in private memory 420 is self-verified by a data verifier 422 so that what's stored can be trusted as reliable. Parts of private memory 420 can be read in or written out to a public memory 430 shared by other smart agents 400. What's stored in public memory 430 may not necessarily be reliable information.

Smart agents 400 never stop training or learning. It therefore does not need to engage in a discrete training period except when the whole are being put to use. Smart processor 406 makes decisions that are forwarded through a release output multiplexer 420 to outputs (01-08) 421-428. The decisions are contrived to advance toward goals 402. How well any generation of decisions do that is tracked in knowledge memory 404. In a sense, such operates like a genetic algorithm. Feedback is needed to assess job performance, and depending on the application, the feedback can be immediate, delayed, partial, inferred, or never forthcoming. Inputs are read in one cycle, decisions made in a next cycle, and outputs released in a third cycle. For example to keep processes synchronized and to eliminate race conditions.

Embodiments of the present invention use compiler tools during development to generate a self-spawning community of smart agents 400 that each maintain an expertise single-mindedly devoted to following the claims behavior of a particular health care healthcare provider. The overall proficiency of the system will be the sum of the abilities of the community of smart agents 400. Adding new smart agents 400 can add new competencies, and each addition does not require a revision of the main program. Each new smart agent auto constructs its own interpreter.

An algorithm can be constituted as:

```
IF (you find this)
    THEN (this)
        ELSE IF (this)
            OR (-switch)
                (-case if)
```

Opinions of experts and business rules and policies can often be used to fill in the blanks here. The IF part inputs the data 411-418. The THEN part represents the optimum response. Goal-oriented smart agents can determine what kind of information is good or bad or in favor or disfavor with a global or local goal 402. This automatically allows smart agents 400 to make the "right" decisions. (The right decisions are those that advance toward the goal.)

Goals 402 can be assigned to smart agents without having to programming them. Complex problems are solved without having to dictate how to solve them exactly. Each smart agent 400 in a group of agents has an expertise that compliments the others, to find an overall balance.

Smart agents can adapt both themselves and influence relationships in their environments. Each possesses a partial representation of the environment. Its behavior is the outcome of its observations, knowledge, and interactions. Answer resolutions result from communications between related smart agents. With a non-algorithmic technology there is no need of exploration of the space of states. The resolution of a problem will emerge as a side effect of the communication between smart agents. Smart agents reach a global objective through interaction: cooperation, concurrence, and conflict resolutions.

Smart agents only have a partial vision of other smart agents they have some relationship with. This vision is tied to the nature of the messages exchanged between the smart agents. The smart agent's environment is its base of observation regarding the global system, this environment reflects the knowledge that the smart agent possesses of its milieu. The environment is to a smart agent what the base of facts is to a knowledge-based system. It represents everything that the smart agent considers true, generally the information is values taken by smart agents, attributes, or even attributes of smart agents. The environment is dynamic because in general it is filled uniquely with the exchange of messages between smart agents.

The information stocked in a smart agent's environment can have a temporary validity (contain an amount of validity), which gives the system the possibility to proceed to a temporal collecting of garbage. It is just as preferable to associate to each piece of information its provenance and its expeditor before being able to judge the credibility of the information. It is the smart agent who must decide what information will be maintained in its environment.

The environment can be divided into public and private zones. All of the smart agents of the systems have the authorization to write in the public zone to make information generally available to certain smart agents. The smart agents are finally free from the recipients of the information to do what they would like. If a smart agent discovers an interesting piece of information in the public zone of its environment, it can transfer such information to its private zone, after validating it.

Each smart agent maintains control of information in its private zone, information the smart agent has validated. Be careful, however; nothing proves to be exact. Only smart agents with the private zone addresses can write to a private zone.

While each smart agent advances toward its goals, it can make observations about its environment that may be useful to other smart agents. That equates to a request for information from a smart agent which is going to respond by placing in the private zone of the requesting smart agent's environment. The information will be translated in the public zone of the smart agent's environment, free from the receiving smart agent in order to understand it, while making the information pass from the public zone to the private zone.

In an organization, the goal of smart agents is to advance the organization's result, without worrying about the means to carry it out. Only one mailbox can be associated with all of the members of the organization to reduce the number of messages. The organization identifier plays the role of supervisor for the member smart agents of the organization. A benefit is derived from the competencies of all the member smart agents without having to remember the addresses of each the smart agents of the organization. Only the organization's identifier address is important.

Smart agents can be organized to work in groups, putting their diverse knowledge together and collaborating toward a common objective. The same information can be viewed from many different perspectives, depending on the questions involved.

The elections made by one smart agent do not propagate to any other smart agent until a next cycle. Thus, all move at the same time.

The messages exchanged between smart agents can be different in age, priorities, and their semantics.

An approach based on learning can be built in three steps: 1. disassembly 2. comparing the parts 3. re-assembly. The power of disassembling lies in the fact that every element of the information system will know how to individually situate itself regarding the others. The group of components can be reassembled in real time at any given moment. The power of evaluate supposes that the system, by nature, has the ability to dynamically position all of the components based on positive or negative inputs. The power of comparing the parts supposes that each element is capable of quantifying its value in relation to the current situation. The conception of each smart agent can be performed independently of the others, since each smart agent only affects others by the fact that they are in favor or disfavor of one of the goals of a smart agent.

At least nine different classification technologies are combined in embodiments of the present invention in a novel way. These technologies include smart-smart agents, real-time profiling, long-term profiling, recursive profiling, business rules, fuzzy technology, neural network algorithms, case-based reasoning, genetic algorithms, data mining, and adaptive learning. The several technologies are allied into one cohesive whole to cooperatively model, personalize, individualize, group, compare, and profile the behaviors of individuals and institutions according to their respective locations, specialties, seasons, time, month, year, place, neighborhood, and other normalizing measures.

Fraud detection reduces to watching for and alerting on unexpected or unexplainable deviations of individuals and institutions from their respective normalized behaviors. A normal behavior slack allows for expected deviations to occur without concern, but an excursion beyond an inner boundary is a call for special attention and extra vigilance. Any excursion beyond an outer boundary of normalized behavior raises a flag for immediate action.

Traditional management-by-exception (MBE) typically brings only actual results information that deviates significantly from the budgeted or planned results to the management's notice. MBE's objective is to enable a thin layer of management to control, a broad organization by focusing scarce management talents on the really important tactical and strategic issues. Any decisions that cannot be made at one level of management are kicked up to the next higher level for action.

Embodiments of the present invention are therefore a form of computer automated MBE that depends on artificial intelligence.

Conventional management by exception has both general business applications and business intelligence applications. The first look for deviations from the normal behavior in a business process, a process deviation, an infrastructure or connectivity issue, an external deviation, poor quality business rules, malformed data, etc. Management by exception here investigates, resolves, and addresses the exceptions with skilled staff and software tools.

Management by exception in business intelligence focusses on and analyzes statistically relevant anomalies in the data. All data is recorded, but only the data that deviates from what is expected or standard need be brought to the attention of the managers. Management by exception can highlight business errors and oversights and spotlight the ineffective strategies that need to be improved. It can help show subtle, easy to miss changes in competition and business opportunities. Management by exception can reduce management workloads, so they can spend their time more effectively in ways it will have the most impact.

Embodiments of the present invention provide a comprehensive solution to health care waste and abuse. SaaS implantations involve themselves in issue identification, qualification, categorization, aggregation, and resolution. Raw datastreams coming from individual healthcare providers and institutions are run through an SaaS to identify risk and high variance issues. The data is not limited to claims, it also includes non-claims based utilization data, or actual clinical data from an EMR, Pharmacy claims, or other transactions. Qualification of the individual risk or scoring event.

The SaaS includes a dashboard to list the opportunities, any recoveries possible, and ways to prevent the same later.

The Diagnosis-related group (DRG) is an accounting system used to classify hospital cases into one of originally 467 groups, with the 467th group being "Ungroupable".

Predictive models monitor the target behaviors using form data reported within form data fields from a Patient History.

A healthcare fraud prevention system will usually have reliable identifications of the sources of fraudulent data and the corresponding deceitful activities. Here, the fraudsters are legitimate individual healthcare providers and institutions but only behaving in duplicitous ways. On the surface, who they are and what they do appears authorized and rational. With credit card fraud, for example, it is the real identity of the fraudster that is obscure, and they are able to abscond immediately and not wait for a check on an invoice months later. The legitimate individual being victimized is completely innocent.

| PATIENT HISTORY |
| --- |
| Date patient was admitted to facility |
| Date patient was discharged from facility |
| Indicates the source of the admission |
| Physician referral/newborn |
| clinic referral |
| HMO referral/sick baby |
| Transfer from hospital/extramural birth |
| Emergency Room |
| Law enforcement |
| Other |
| Describes the admission of the patient to the facility: |
| Emergency |
| Elective |
| Newborn |
| Pending Medicaid eligibility |
| Admission denied |
| Transfer |
| Rehabilitation |
| Transferee returned |
| Indicate patient's destination upon discharge from facility: |
| Home |
| Transfer to hospital |
| Transfer to other |
| Transfer to home/HSO |
| left against medical advice |
| transfer to distinct psych unit |
| expired |
| still patient |
| died at home (hospice) |
| died at facility |
| died, place unknown |
| rehabilitation transferred with DRG |
| Patient gender |
| Patient date of birth |
| The dollar amount paid to the healthcare provider for a particular DRG |
| Total charge amount - the dollar amount charged by the facility for a particular DRG |
| Diagnosis Related Group - a three-digit code that organizes diagnoses and procedures into clinically cohesive groups that demonstrate similar consumption of hospital resources |
| Primary diagnosis code |
| Secondary diagnosis code |
| Third diagnosis code |
| Fourth diagnosis code |
| Fifth diagnosis code |
| Primary procedure |
| Secondary procedure code |
| Third procedure code |

A healthcare fraud prevention system will usually have reliable identifications of the sources of fraudulent data and the corresponding deceitful activities. Here, the fraudsters are legitimate individual healthcare providers and institutions but only behaving in duplicitous ways. On the surface, who they are and what they do appears authorized and rational. With credit card fraud, for example, it is the real identity of the fraudster that is obscure, and they are able to abscond immediately and not wait for a check on an invoice months later. The legitimate individual being victimized is completely innocent.

Diagnosis-related group (DRG) is a system to classify hospital cases into one of originally 467 groups. The 467th group is "Ungroupable". The intent was to identify the "products" that a hospital provides. The system was developed in anticipation of convincing Congress to use it for reimbursement, to replace "cost based" reimbursement that had been used up to that point. DRGs are assigned by a "grouper" program based on ICD (International Classification of Diseases) diagnoses, procedures, age, sex, discharge status, and the presence of complications or comorbidities. DRGs have been used in the US since 1982 to determine how much Medicare pays the hospital for each "product", since patients within each category are clinically similar and are expected to use the same level of hospital resources. DRGs may be further grouped into Major Diagnostic Categories (MDCs). DRGs are also standard practice for establishing reimbursements for other Medicare related reimbursements such as to home healthcare providers.

Assigning a DRG requires skill, is susceptible to mistakes, and is a ripe area for fraud. A wrong categorization can make a difference in thousands of dollars. Patients recovering unexpectedly well from serious DRG's could be seen as fortunate on one hand, or vessels of opportunity to get a few extra bucks and a pat on the back for a "win". A smart agent to detect DRG abuses would correlate the individual doing the DRG categorization and the patients' subsequent treatments and survival. Mistakes tend to be random, fraud never is.

The Centers for Medicare & Medicaid Services (CMS) system re-sequenced the DRG groups in 2007, "Ungroupable" is no longer Group 470 but changed to 999. The newly re-sequenced DRG are now known as MS-DRG. Before the introduction of version 25, many CMS DRG classifications were "paired" to reflect the presence of complications or comorbidities (CCs). A significant refinement of version 25 was to replace this pairing, in many instances, with a trifurcated design that created a tiered system of the absence of CCs, the presence of CCs, and a higher level of presence of Major CCs. As a result of this change, the historical list of diagnoses that qualified for membership on the CC list was substantially redefined and replaced with a new standard CC list and a new Major CC list. Another refinement was not to give strict sequenced numbers to the DRG's, as compared with the prior versions. In the past, newly created DRG classifications would be added to the end of the list. In version 25, there are gaps within the numbering system that will allow modifications over time, and also allow for new MS-DRGs in the same body system to be located more closely together in the numerical sequence. Other version changes have occurred since 2007.

California Statutes from October 2010 added Section 14105.28 to the Welfare and Institutions Code which mandated the design and implementation of a new payment methodology for hospital inpatient services provided to Medi-Cal beneficiaries based upon diagnosis related groups (DRGs). Payment by DRGs encourages access to care, rewards efficiency, improves transparency, and improves fairness by paying similarly across hospitals for similar care. Payment by DRGs also simplifies the payment process, encourages administrative efficiency, and bases payments on patient acuity and hospital resources rather than length of stay. (That is, of course if no errors have been made in the initial assignment of a DRG.)

Effective Jul. 1, 2013, in California, the DRG payment methodology replaced the previous payment method of negotiated rates for contract hospitals and cost-based reimbursement for non-contract hospitals. Per diem rates for contract hospitals were negotiated by the former Office of the Selective Healthcare provider Contracting Program (SPCP) and the California Medical Assistance Commission (CMAC). The SPCP or contract hospital reimbursement was established legislatively in 1982 and operated under a federal waiver.

Non-contract hospitals were reimbursed based on Medi-Cal allowable, audited costs. Hospitals were paid interim rates using a cost-to-charge ratio based on the most recently submitted cost report. A cost settlement process reconciled the difference between interim payments and the allowable costs of providing services.

The Prior Art is familiar with various analytical fraud detection. ACL Services Ltd. (Vancouver, BC) published a Whitepaper that says getting started requires an understanding of:

The areas in which fraud can occur;
What fraudulent activity would look like in the data; and,
What data sources are required to test for indicators of fraud.

ACL says the following analytical techniques are effective in detecting fraud:

Calculation of statistical parameters (e.g., averages, standard deviations, high/low values) - to identify outliers that could indicate fraud;
Classification - to find patterns amongst data elements;
Stratification of numbers - to identify unusual (i.e., excessively high or low) entries;
Digital analysis using Benford's Law - to identify unexpected occurrences of digits in naturally occurring data sets;
Joining different diverse sources - to identify matching values (such as names, addresses, and account numbers) where they shouldn't exist;
Duplicate testing - to identify duplicate transactions such as payments, claims, or expense report items;
Gap testing - to identify missing values in sequential data where there should be none;
Summing of numeric values - to identify control totals that may have been falsified; and
Validating entry dates - to identify suspicious or inappropriate times for postings or data entry.

Random sampling is not listed as an effective fraud detection technique. While sampling is an effective data analysis technique for analyzing data values that are consistent throughout the data population, the very nature of fraud is different as it tends not to occur randomly.

What the Prior Art does not appreciate or contend with is all frauds are different, especially new strategies that developed from the older, less successful ones. Many are quite secret and never discovered. Some are modest and others are extreme. Others are systematic and conducted by organizations and networks, and some are single point.

Both good and bad behaviors and their environments evolve over time and they adapt to new rules, treatment options, new pharmaceuticals, new Laws, and changing attitudes of the patients, individual healthcare providers, institutions, and insurance companies. Self-defining and self-correcting behavioral models can keep pace with such changes, and do it without a catastrophe prompting a change in the programming. Fraud also works predictably for the fraudster, they always gain. Mistakes and sea changes are neutral over time.

Physicians, nurses, specialists, and other health care professionals are paid in different ways, depending on the nature of their positions, the work, and the facility. Each pay rate is assigned a unique electronic code. These codes can be pulled for staff members, e.g., those working on-call. Understanding what would comprise accurate coding can be used to set up behavioral constraints and exceptions, e.g., the maximum number of consecutive hours one can spend on-call. Audit analytics can be used to pull the employee records to run the data through a script. This method can identify abusive staff members. e.g., those who had supposedly worked on-call an impossible 24-hours a day, seven days a week. Or those who were paid for on-call time while they were away on vacation. Such a straightforward data analysis can be used to highlight time and attendance fraud.

Here are a few typical fraud schemes encountered in healthcare and some examples of the way data analysis can be applied to detect and prevent them: Match Office of Inspector General (OIG)-excluded healthcare providers list with vendor, employee master files. Find kickbacks paid in exchange for referring business. Identify charges posted outside of proper GL period. Highlight "upcoding" of procedures: Statistically outlying numbers. Match vendor names/addresses/tax IDs to payroll records for employees. Summarize large invoices without purchase orders, by amount, vendor, etc. Compare list of valid signed-up employees to list of people actually receiving health benefits from insurance company. Highlight billing for medically unnecessary tests. Identify false/invalid/duplicate Social Security numbers. Highlight excessive use of high risk DRG's. Identify excessive billing by a single physician. Identify employee overtime abuses. Report entries against authorization records for new or terminated employees. Identify multiple payroll deposits to the same bank account.

Embodiments of the present invention create a virtual smart agent for each healthcare industry healthcare provider. Each such virtual smart agent is configured to observe and learn the behavior of its host healthcare industry healthcare provider over time to create a user profile. The ways the healthcare industry healthcare provider functions, the frequency of their activities, the types of actions taken, e.g., during the last minute, ten minutes, over days/weeks/years are all intelligently aggregated into a profile of what's normal for this healthcare provider.

In a "REPORT TO THE NATIONS ON OCCUPATIONAL FRAUD AND ABUSE" in their 2012 GLOBAL FRAUD STUDY, The Association of Certified Fraud Examiners analyzed 1,388 cases of occupational fraud. Ninety-two of these cases were related to health care fraud. The number one class of fraud was in billing, followed by corruption, expense reimbursements, and skimming. These are all the very sorts of behaviors SaaS embodiments of the present invention can flag for law enforcement and auditors.

| Health Care 92 Cases | | |
| --- | --- | --- |
| Scheme | Number of Cases | Percent of Cases |
| Billing | 33 | 35.9% |
| Corruption | 28 | 30.4% |

-continued

Health Care 92 Cases

| Scheme | Number of Cases | Percent of Cases |
| --- | --- | --- |
| Expense Reimbursements | 19 | 20.7% |
| Skimming | 18 | 19.6% |
| Check Tampering | 17 | 18.5% |
| Non-Cash | 17 | 18.5% |
| Cash Larceny | 16 | 17.4% |
| Payroll | 14 | 15.2% |
| Cash on Hand | 14 | 15.2% |
| Financial Statement Fraud | 9 | 9.8% |
| Register Disbursements | 6 | 6.5% |

There are a number of behavioral flags that can be used by auditors and management to detect fraud. Those identified by the Association of Certified Fraud Examiners vary according to job function. Most would not be something a computer could be expected to recognize on its own without some kind of artificial intelligence and assistance.

In Accounting

| Behavioral Flag | % of cases |
| --- | --- |
| Living Beyond Means | 43.7% |
| Financial Difficulties | 30.4% |
| Control Issues/Unwillingness to Share Duties | 19.5% |
| Divorce/Family Problems | 18.8% |
| Irritability, Suspiciousness or Defensiveness | 12.6% |
| Addiction Problems | 11.3% |
| Refusal to Take Vacations | 10.9% |
| Complaining About Inadequate Pay | 6.5% |
| Past Employment-Related Problems | 6.5% |
| Unusually Close Association with Vendor/Customer | 6.1% |
| Past Legal Problems | 5.8% |
| Wheeler-Dealer Attitude | 5.1% |
| Instability in Life Circumstances | 4.4% |
| Excessive Family/Peer Pressure | 3.8% |
| Complaining About Lack of Authority | 3.4% |

In Upper Management

| Behavioral Flag | % of cases |
| --- | --- |
| Living Beyond Means | 49.1% |
| Wheeler-Dealer Attitude | 32.1% |
| Control Issues/Unwillingness to Share Duties | 26.4% |
| Financial Difficulties | 25.2% |
| Unusually Close Association with Vendor/Customer | 22.6% |
| Divorce/Family Problems | 13.8% |
| Irritability, Suspiciousness or Defensiveness | 13.2% |
| Past Employment-Related Problems | 11.9% |
| Addiction Problems | 10.7% |
| Excessive Pressure from within Organization | 10.1% |
| Past Legal Problems | 8.2% |
| Excessive Family/Peer Pressure | 6.9% |
| Complaining About Lack of Authority | 6.3% |
| Complaining About Inadequate Pay | 5.7% |
| Refusal to Take Vacations | 4.4% |
| Instability in Life Circumstances | 3.8% |

Other technologies can be usefully combined with smart agents to produce even better results. Neural networks are a kind of algorithmic system that can interpret historical data and help identify trends and patterns against which to compare subject cases. Neural networks have the remarkable ability to solve problems related to detecting trends and patterns that humans or other computer techniques are unable to solve.

An Artificial Neural Network (ANN) models the ways in which biological nervous systems process information. The brain, e.g., consists of billions of processors, which process a large number of tasks concurrently. Neurons work collaboratively to solve the defined problem. Neural networks can resemble human reasoning, making them well suited to solve pattern recognition and forecasting problems.

ANN's have two primary parts, neurons, represented by neural units; and, synapses, connections between the neurons, which send signals from neuron to neuron. Those synapses can be excited (positive weight), or inhibited (negative weight). Most known neural networks have input layers for the smart agent to receive data from the environment, and output layers for the smart agent's potential actions. Others (like Back Propagation) have one or more intermediate layers between these two layers. These layers are massively interconnected, as the units on one layer are connected to those in the next layer. Just like the factors that shape a human, the factors that shape a neural network are its environment and its genetic makeup. Both its initial state and its training play a role in the ANN's development. It is through the critical training process that ANN's are taught how to arrive at the correct answer. A well-trained neural network will be more successful than a poorly trained neural network. The training refers to its environment and the experiences and samples that help shape it. The more samples and experience a neural network receives has a direct correlation with its likelihood of its success.

Case-based reasoning (CBR) can use past experiences or cases to solve new problems. Each "case" is translated into a list of steps to lead to a desirable outcome. The cases are stored and organized in a database, and used as an index for similar situations later. Solutions to complex problems can be found very quickly and accurately this way.

Being able to retrieve and manipulate past problem-solving examples accurately is important. Case-based systems search their case memories for an existing cases that match the input "specifications". As new cases are solved, the solutions are added to the case memory. Such will continue to grow the database of cases solved and increase the likelihood of success.

The goal is to find a case that matches the input problem and that proceeds directly to a solution. Thus making it possible to provide solutions to potentially complex problems quickly. If, on the other hand, an exact match cannot be found, the case-based system look for a similar one to the input situation, and then offer it as a potential solution.

How the system learns is when a nonperfect match is found that nevertheless solves the problem, the case is added to the systems case memory for future use. Each case is a recipe of steps that will lead to a particular outcome. A case is a connected set of subcases that form the problem-solving task's structure.

One of the key differences between rule-based and case-based knowledge engineering is that automatic case-indexing techniques drastically reduce the need to extract and structure specific rule-like knowledge from an expert. CBR systems retrieve relevant cases quickly and accurately from its memory. When a case should be selected for retrieval in similar future situations is the goal of case-indexing processes. As cases accumulate, case generalizations can be used to define prototypical cases that can be stored with the specific cases, improving the accuracy of the system in the long run.

The inductive-indexing capabilities in CBR systems provide several major advantages over neural networks and pattern-recognition techniques. Inductive systems can represent and learn from a wider range of feature types than either neural networks or pattern recognition. The ability to use richer feature sets for describing examples makes them at least as accurate and many time more precise. Case-Based Reasoning solves complex problems like planning, scheduling, and design by finding a similar, successful past plan, schedule, or design, and modifying it to meet the current problem's needs.

Another technology that can be added in a combinational approach is Fuzzy Logic. Fuzzy logic is able to account for areas that are not clearly defined. The logic can be extended to handle partial truths in situations where the answer lies somewhere in between what is true and what is false. Many of the big problems in organizations cannot be solved by simple yes/no or black/white programming answers. Sometimes answers come in shades of gray, where fuzzy logic proves useful. Fuzzy logic handles imprecision or uncertainty by attaching various measures of credibility to propositions. Fuzzy technology enables clear definition of problems where imperfect or partial knowledge exists, such as when the goal is "about 12 years old" or between "all" and "nothing". Traditional and classical logic typically categorize information into binary patterns such as: black/white, yes/no, true/false, or day/night.

The power of fuzzy logic is exponential when it is combined with other technologies like genetic algorithms, neural networks, and business rules. Many of the big problems in organizations cannot be solved by simple yes/no or black/white programming answers. Sometimes answers come in shades of gray, this is where fuzzy logic proves useful. Fuzzy logic handles imprecision or uncertainty by attaching various measures of credibility to propositions.

Genetic algorithms are able to address complicated problems with many variables and a large number of possible outcomes, by simulating the evolutionary process of "survival of the fittest" to reach a defined goal. They operate by generating many random answers to a problem, eliminating the worst and cross-pollinating the better answers. Repeating this elimination and regeneration process gradually improves the quality of the answers to an optimal or near-optimal condition. In computing terms, a genetic algorithm is a population of individuals represented by chromosomes, a set of character strings.

Genetic algorithms include three stages: building and maintaining a population of solutions to a problem, choosing the better solutions for recombination with each other, and using their offspring to replace poorer solutions. Each stage produces a new generation of possible solutions for a given problem.

In the first stage, an initial population of potential solutions is created as a starting point for the search process, each element of the population is encoded into a string (the chromosome), to be manipulated by the genetic operators. In the next stage, the performance (or fitness) of each individual of the population is evaluated with respect to the constraints imposed by the problem. Each individual of a population represents a possible solution to a given problem. Each individual is assigned a "fitness score" according to how good a solution to the problem it is. A potential solution to a problem may be represented as a set of parameters.

Business Rules, or Expert Systems are the most widely used commercial applications developed using artificial intelligence (AI). Many use expert systems to solve business problems. Expert systems model information at a higher level of abstraction. When these systems are implemented well they closely resemble human logic and become more reliable and easier to maintain. The goal is for the expert system to apply heuristic knowledge to give advice or make recommendations just like a human expert. Rules are used to represent a rule-of-thumb to specify a group of actions performed for a given situation. Rules are composed of IF-THEN statements that comprise the necessary solution. An inference engine automatically matches facts against patterns and automatically determines which rules are applicable. This process of selecting rules against historical patterns will continue to repeat itself until no applicable rules remain. It is critical that the knowledge source is reliable, because the system is only as good the knowledge assimilated into the rules. One of the most difficult tasks in developing an expert system is extracting the knowledge from an expert so the rules can be written. The most widely known algorithms for compiling rules are RETE and TREAT.

Data mining, or knowledge discovery, in databases is the nontrivial extraction of implicit, previously unknown and potentially useful information from data. It is the search for relationships and global patterns that exist in large databases but are hidden among the vast amount of data. Using particular classifications, association rules and analyzing sequences; data is extracted, analyzed and presented graphically. Data mining, or knowledge discovery in databases is the nontrivial extraction of implicit, previously unknown and potentially useful information from data. It is the search for relationships and global patterns that exist in large databases but are hidden among the vast amount of data. Using particular classifications, association rules and analyzing sequences, data is extracted, analyzed and presented graphically.

Data mining algorithms always requires a number of different technical approaches to address data cleaning, sampling, clustering, learning classification rules, analyzing changes and detecting anomalies.

Descriptive Statistics is the process of obtaining meaningful information from sets of numbers that are often too large to deal with directly. While it is often impossible to calculate scores for all models when searching a large model space, it is often feasible to describe and calculate scores for a few equivalent classes of models receiving the highest scores. Prediction methods for this sort of problem always assume some regularity in the probability distribution.

Real-time profiling keeps track of activities over windows time spanning seconds, minutes, hours, days, months or even years. These profiles can highlight suspicious changes in healthcare provider activities, by looking at the number of transactions from a healthcare provider over a window of time, histories of payment methods, typical purchasing from the healthcare provider, patterns and clickstreams of the healthcare provider at the merchant's site, e-mail address activity from the healthcare provider, ship-to and bill-to activity, etc.

Smart Agent for Billings-for-Services-not-Rendered

In many cases where medical healthcare providers and facilities have submitted claim forms to government health care plans and insurance companies for services and care that were never provided, there will a lack of supporting documentation in the corresponding patient files. The reported dates of service listed on the claim forms can act as a starting point to look for documentary evidence that the supposed patients were at the facility on the relevant dates. The patient's medical files are check, if a staff member had seen the patient, somebody should have written something down. Even if it was just taking the patient's height, weight, and blood pressure. The facility's sign-in logs and appointment calendars can also be used to verify if the patient was present.

A behavioral pattern of billing for services and care with no supporting documentation is indicative of fraud. And so a smart agent can be assigned to track each healthcare provider's billing patterns to build statistics on what is normal for this healthcare provider, and those results can be compared to similar healthcare providers in similar situations.

Smart Agent for Billings-for-a-Non-Covered-Service-as-a-Covered-Service

Some treatments are considered experimental and therefore not approved by government health care plans or other insurance companies. With a few taps on a keyboard, a healthcare provider can nevertheless submit claim forms and still get paid by coding it as something else that was covered by insurance plans and policies. Unusual behaviors can be looked for in the patients' files, e.g., reporting that patients were treated at an allergy clinic four or five days per week. More likely they only received injections twice a week.

Smart Agent for Misrepresentations-of-the-Dates-of-Service

Healthcare providers can bill more by reporting they visited or and treated the same patient on two separate days rather than one day. Each "office visit" is usually considered a separate billable service. Often the services the fraudsters list on claim forms are actually provided, but the dates are false because it's more profitable for the healthcare providers. A comparison with the corresponding patients' medical files to see if they match the dates of service listed on the claim forms.

Smart Agent for Misrepresentations-of-Locations-of-Service

Examination of the claim forms will tell where the services were allegedly performed. Billings for services on Saturday, Sunday or holidays, when most clinics are closed, can raise questions. Billing for services provided by doctors in their offices in the U.S. while the physicians were actually on overseas vacations should also be a trigger.

Smart Agent for Misrepresentations-of-the-Healthcare Provider-of-Service

Sometimes employees impersonate a physician and bill for treatment. Medical doctors sometimes sign insurance claim forms showing that they had provided all the care, but in reality, lesser-educated health professionals actually conducted the therapy and would have been paid less.

Smart Agent to Detect Waiving-of-Deductibles-and-Copayments

Most government health care plans and insurance companies don't allow medical healthcare providers or facilities to waive patients' deductibles or co-payments. The rationale being if patients have to pay something to see the doctors, the patients will only seek care only in more severe cases. Some healthcare providers waive patients' deductibles or co-payments and then submit false billings to insurance companies to make up the dollar difference. Really deceitful healthcare providers also heap more false services onto the claim forms to further increase their illegal gains. (The patients are unlikely to complain because their co-payments and deductibles were waived.)

The medical facilities' financial records should show payments of the co-payments and deductibles. The patients can also have copies of receipts, cancelled checks, or credit card receipts showing what they paid.

Smart Agent to Detect Incorrect-Reporting-of-Diagnoses-or-Procedures

Listing an incorrect, but more costly, diagnosis or procedure is one way to up the billings. Some diagnoses require admission and longer, more expensive hospital stays. Instances where patients suddenly "got better" as soon as their insurance coverage ran out should be cause for deeper examination. One of the most popular incorrect reporting of procedures is unbundling. Simple unbundling occurs when a healthcare provider charges a comprehensive code plus more component codes.

Smart Agent to Detect Unnecessary-Services

Billing for services that aren't really necessary can be used on hypochondriac patients. Tests and exams can go on indefinitely or at least as long as a patient still has coverage or is able to make payments. Alcohol and drug rehabilitation facilities are ripe for overutilization.

Smart Agent to Detect Corruption, Kickbacks, and Bribery

Healthcare providers have been known to unlawfully pay for and receive payment for referrals for services that aren't even needed, such as X-rays, MRIs, prescription drugs, etc. Every bribery/kickback scheme involves a quid pro quo ("this for that"). The smart agent looks for correlations between what the healthcare provider paid or received something of value in return for the referrals. Sometimes the kickbacks or bribes are hidden or disguised in the form of luxury vacations, discounts on facility rentals or hidden gifts as compared to just slipping a check or cash under the table.

Smart Agent to Detect False-or-Unnecessary-Issuance-of-Prescription-Drugs

Prescription drug abuse involves taking prescription medication for reasons beyond physicians' intentions. Painkillers are the most commonly abused prescriptions. The street value is ten times the legal prescription value. Some patients "doctor shop" to obtain drug prescriptions, especially painkillers. The doctors usually have no idea that the patients have already visited other physicians to obtain the same or other drugs. Fraudsters can easily recover the cost of the doctors' visits and filling of prescriptions by selling some or all of the drugs on the street. Some patients, and even medical facility employees, have been known to steal prescription paper pads and forge prescriptions and healthcare provider signatures. Others make pen-and-ink changes to the quantity and authorized refill numbers on the paper prescriptions. (Electronic prescriptions from healthcare providers to pharmacists are helping prevent this fraud.) Claims can only be submitted, processed and paid when all of the required protected identifying information (PII) is listed on the claim forms. That PII will include the patient's name, date of birth, insurance policy number, and Social Security number. PII is the key, without it, no claim will be paid. "Patients" whose names are listed on the claim forms should not be assumed to actually received anything. A cautious fraudster may simply include a few low-dollar false billings on several different patient claim forms to stay under the radar. Small-dollar claims listed under individual patient names should not be dismissed because they could be part of a higher-dollar fraud scheme. The names are important data that shouldn't be overlooked. A crooked pharmacist can alter the quantity listed on legitimately received prescriptions for painkillers, manipulate the patients' paperwork and receipts, or make the co-payments themselves and steal the extra drugs. The possibilities are endless.

Figure 5:
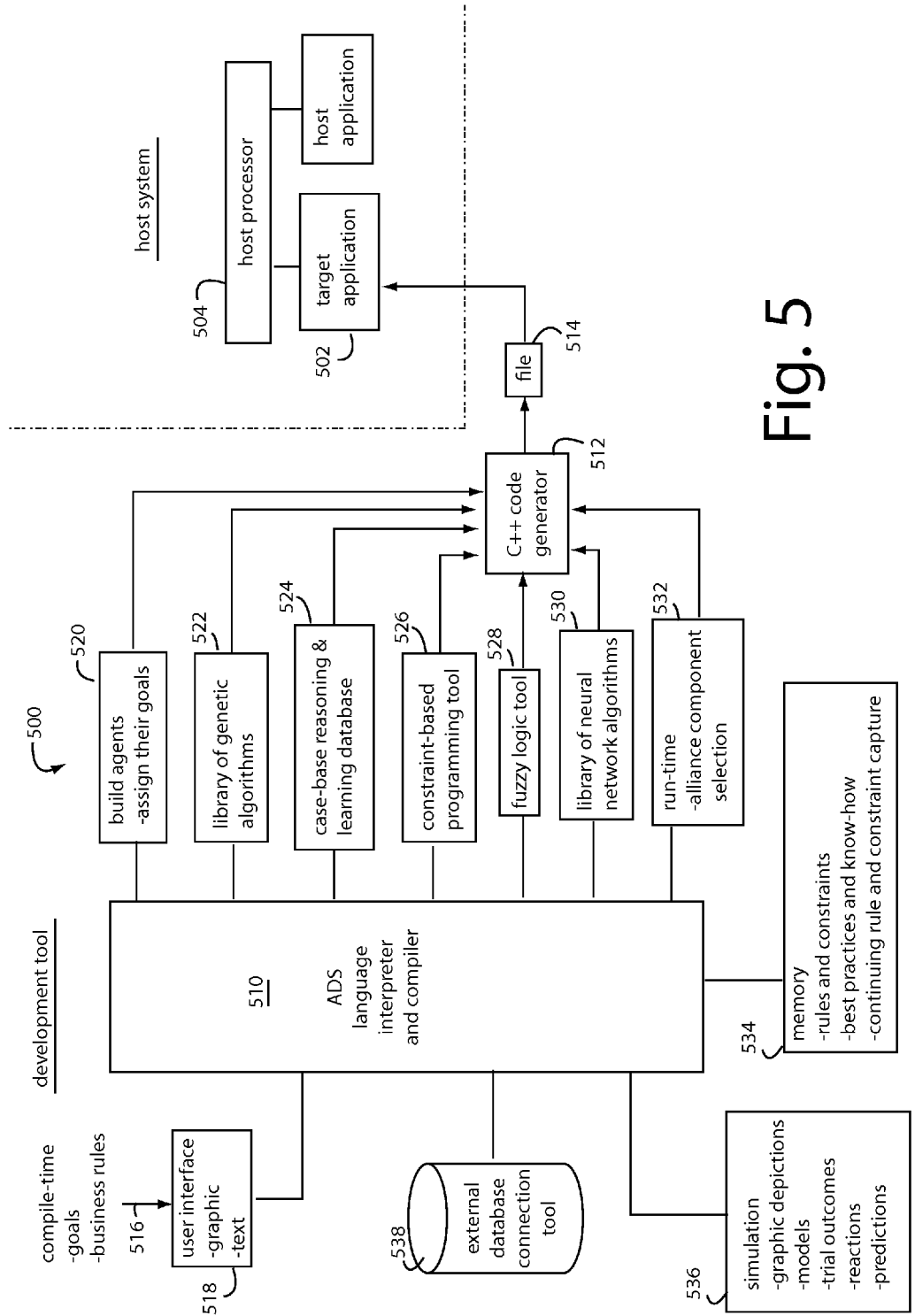
FIG. 5 is a functional block diagram of such a specialized compiler and development system tool useful in the development of target applications for fraud detection in medical claim processing.

FIG. 5 represents an applications development system (ADS) 500 for defining, building, and producing multi-agent software-as-a-service (SaaS) target applications 502 that will run on a variety of host processors 504 already in service. For example, like SaaS 200 illustrated in FIG. 2.

ADS 500 includes a declarative language 510 that provides feedback and an evaluation loop during each step of user development.

Each optimization suite, business rule, fuzzy logic, neural network suite, genetic algorithm, cased-based reasoning, data mining, and other classification model technology used here has its own strengths and weaknesses in specific applications. Modern business applications often need a coalition of such technologies that can be combined to form a unified solution. The ADS compiler 510 arranges coalition's components in the target application so they can be selected and scheduled ad hoc at run-time to adapt to a changing environment.

A library of genetic algorithms 522 in C++ code provides ways to rate an existing model and hunt for more efficient strategies to select the attributes that will kept for model training. Genetic algorithms use principles derived from the study of evolution and natural selection to test random deviations. The most productive solutions can be found in terms of money, work, time, or another measures.

A case-based reasoning and learning database 524 is a collection of successfully solved case history experiences of an organization that can be referenced later to resolve repeating similar situations. The mix of successful processes that were used in solving particular problems in the past are what's stored and available to be consulted later. For example, an exception to a general rule that worked in the past could be remembered by the peculiar environment that presented at the time.

The constraint-based programming tool 526 constitutes a very complete language in its own right. It integrates variables with arithmetic, temporal, Boolean, and symbolic constraints. Such variables include real, with integer values, enumerated, sets, matrices and vectors, intervals, fuzzy subsets, etc.

The arithmetic Constraints include $=, +, -, *, /, /=, >, <, >=, <=$, interval addition, interval subtraction, interval multiplication and interval division, max, min, intersection, union, exponential, modulo, logarithm, etc. The temporal (Allen) Constraints allow any temporal constraints to be written including Equal, Not-equal, Before, After, Meets, Overlaps, Starts, Finishes, and personal temporal operators such as Disjoint, Started-by, Overlapped-by, Met-by, Finished-by, etc. The Boolean Constraints can include Or, And, Not, Xor, Implication, Equivalence. And the symbolic Constraints of Inclusion, Union, Intersection, Cardinality, Belonging, etc.

A fuzzy logic tool 528 accommodates for imprecision or uncertainty by attaching various measures of credibility to input propositions that will occur in run-time. A clear definition of problems is nevertheless possible when only inadequate or partial knowledge is available, such as when a goal is given as "about 12 years old", or an amount is between "all" and "nothing". The various measures of credibility to attach are definable in compile-time by the user programmer.

An easy-to-implement library of advanced neural network algorithms 530 includes a collection of technologies useful in run-time to decipher patterns and remember them for future operations. Neural network algorithms are particularly useful in solving problems of identification, forecasting, planning and data mining. Library 530 provides as many as twelve different neural network algorithms, including Back propagation, Kohonen, Art, Fuzzy ART, RBF, etc.

Run-time executive program 532 executes in run-time to coordinate the smart agents and classification models with the goals, constraints, credibility.

Figure 6:
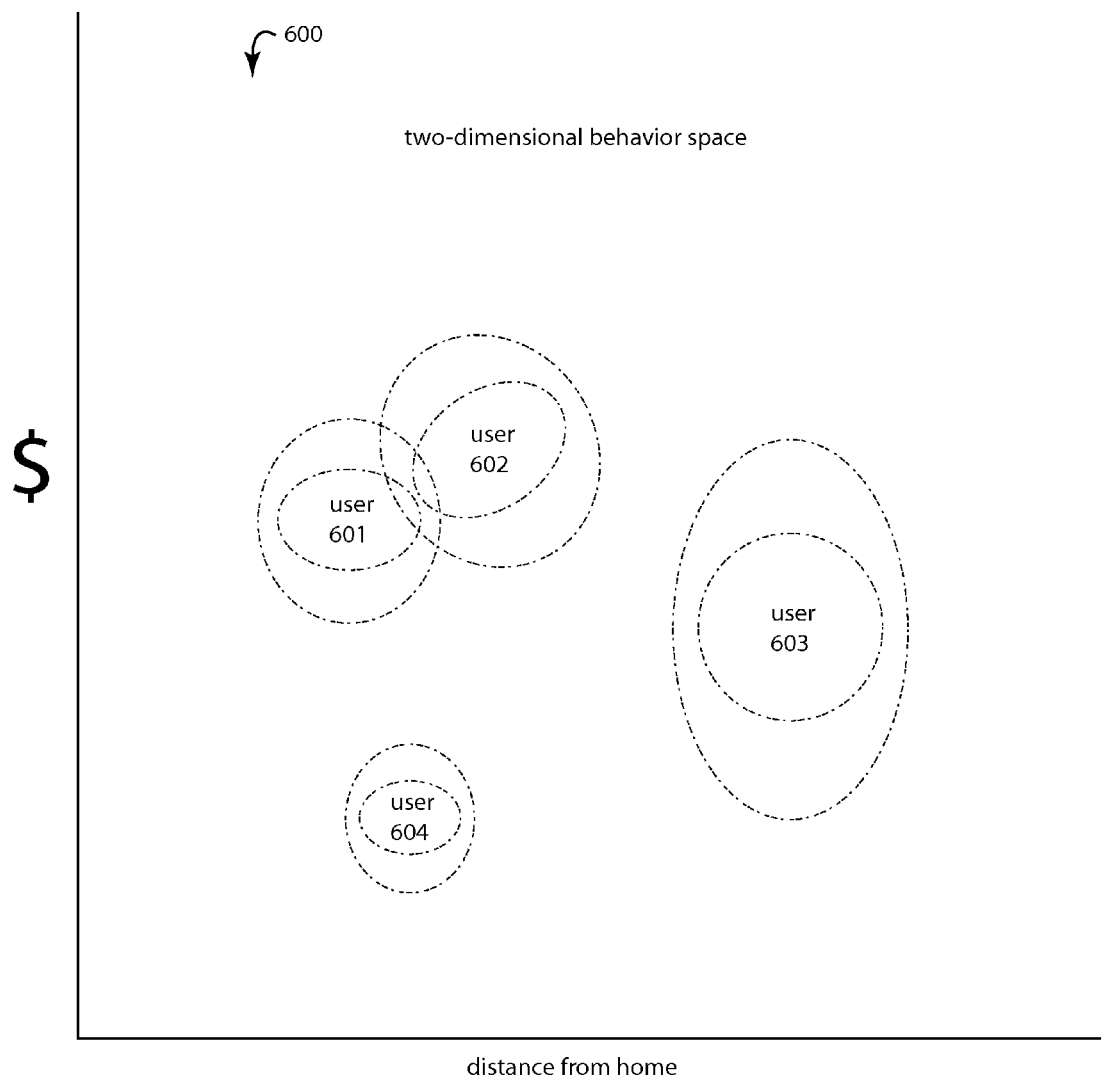
FIG. 6 is a graphical diagram of a two-dimensional user behavior space, and is representative of a multi-dimensional user behavior space that would be practical and affordable to construct with conventional technologies and networks.

Referring to FIG. 6, it is normal for user 601 in one behavioral aspect or facet to venture out less distantly than users 602-504, but still user 601 will typically spend more than user 604. User 603 has the widest range of normal behaviors in these dimensions, and user 604 has the tightest range. FIG. 2 refers to the collection and analysis of behaviors as profiling.

The many other simultaneous dimensions that can be included in user behavior space run the gambit of time-of-day, day-of-week, days-before-holiday, coupon redemption correlations, merchant-by-category, products strongly associated with adult/juvenile men/women, etc.

The engineering of a system that builds the data from transactional information user-by-user and that does boundary monitoring in multi-dimensional spaces is expected to be straightforward for any artisan in this field and a detailed description of how to construct the pieces seems unnecessary here.

Figure 7:
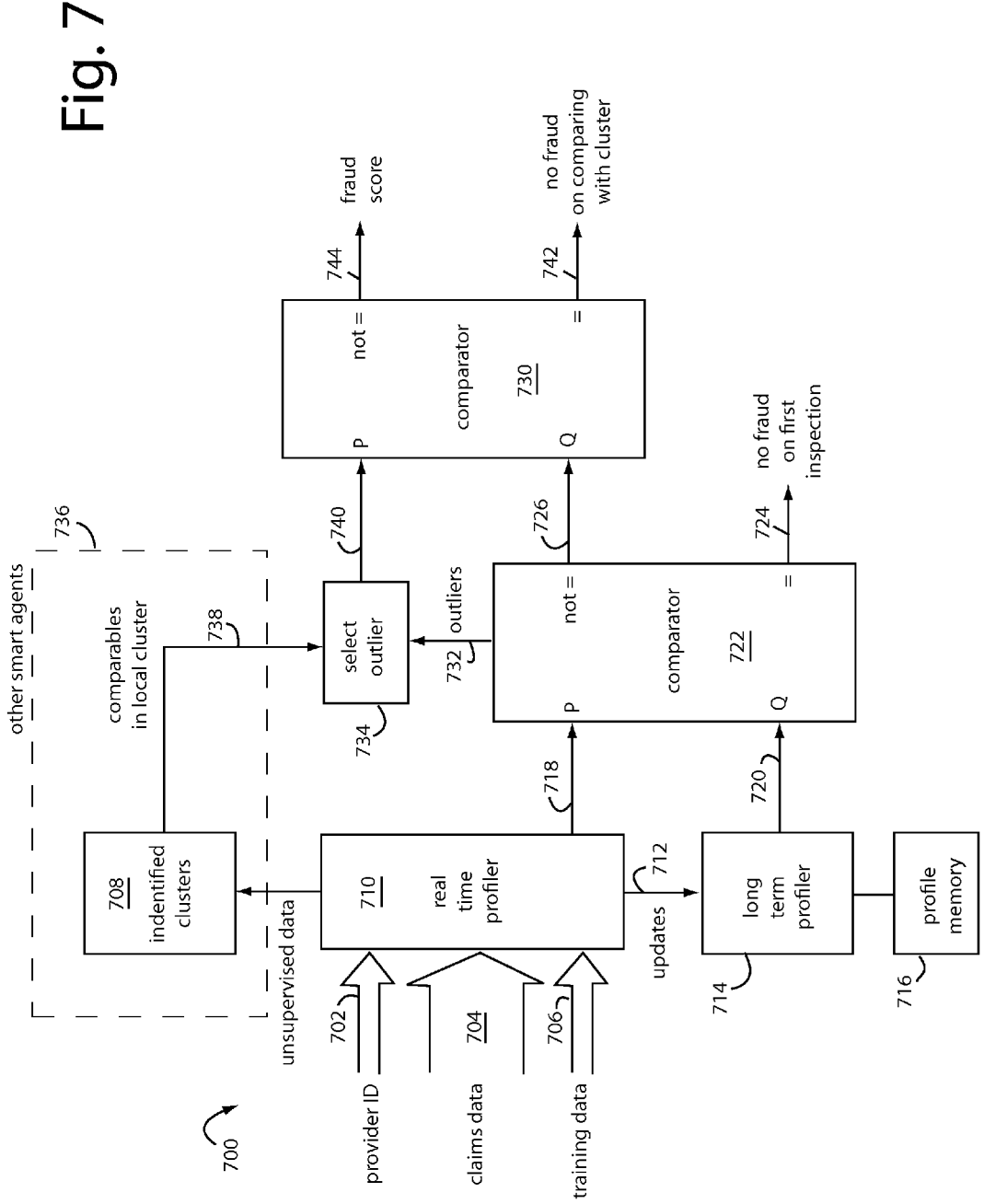
FIG. 7 is a functional block diagram representing how a medical healthcare fraud smart agent can be implemented in hardware.

FIG. 7 represents a hardware implementation of a smart agent 700 in one embodiment of the present invention. More practical, and run-time scalable instances will be implemented with software. A least one smart agent 700 must automatically spawn or be assigned for each individual healthcare provider subject to fraud monitoring. This implies there can be thousands, or even millions of such smart agents 700 in one application.

A healthcare provider ID address 702 uniquely identifies which individual healthcare provider is then supplying a claim data 704. Such claim data 704 is highly detailed and exact as to the particulars of specific claims for payment being presented in real-time. The detail, times the number of healthcare providers, times the number of instances would result in an impossible-to-store volume of information that would at best be impractical for fraud detection use here.

If training data 706 is available it can be used to build cases for case-based-reasoning (CBR), data mining, and long term profile databases. Unsupervised data, e.g., a lack of training data 706, can nevertheless be used to identify clusters of healthcare providers by any of several different dimensions inherent in the claims data 704. Identified clusters 708 are available through smart agent mailboxes and specialized smart agents can be assigned to track the more exotic constituents present in the claims data.

A real-time profiler 710 distills the claims data 704 if the healthcare provider ID 702 matches the healthcare provider assigned to this particular smart agent 700. Such distillation reduces the exact numbers in the claims data 704 to something much fuzzier. For example, in the "expense" dimension for services provided for a particular medical procedure, the incoming claims data 704 would be the exact amount in dollars and cents. But real-time profiler 710 would distill each expenses as being, e.g., exorbitant, expensive, high, moderate, discounted, economic, or cheap. Or by symbols to internally represent each as a range. Medical service, procedure, and Diagnosis Related Group codes can similarly be distilled and reduced into, e.g., office-visit, follow-up, out-patient, surgery, etc. Exact locations by address can be reduced to the zip code, the city, the state, or even the country. Depending on the resolution required.

The entire claim of each healthcare provider and all its details are thereby reduced into a single instance profile having a standard set of descriptors. Each smart agent 700 follows a single healthcare provider, so in the following Table, Profiles 1-3 are profiles obtained from three different instances of claims data 704.

| DESCRIPTOR | PROFILE-1 | PROFILE-2 | PROFILE-3 |
|---|---|---|---|
| healthcare provider level | Doctor | nurse, RN | specialist |
| diagnosis | Cancer | cold | eyes |
| expense | High | cheap | ordinary |
| location | San Francisco | San Jose | Oakland |
| facility | Clinic | office | hospital |
| payor | Insurance | Medicare | HMO |

Each instance of claim data 704 for the matching healthcare provider will produce a profile update 712. These profile updates 712 are accumulated by a long term profiler 714 and will over time represent in a profile memory 716 the range of each dimension belonging to this one healthcare provider.

As claim data 704 arrives for the associated healthcare provider, a real time profile 718 is generated and a long term profile 720 for the dimensions involved are presented to a first comparator 722 at its "P" and "Q" inputs. If the real time profile 718 fits within the bounds of the long term profile 720, first comparator 722 will produce an "=" output 724, indicating no fraud on first inspection.

Otherwise, a "not=" output 726 will be output to the "Q" input of a second comparator 730. This output 726 is not necessarily a binary. An outlier 732 is sent to an outlier selector 734 that identifies the dimension and the profile value that seems to be out-of-whack with the long term profile. It could be that an unusual event, or once in a life-time event has occurred, and there would be not corresponding history of such a thing in the profile memory 716.

However, some other smart agent 736 may have had a comparable experience inside the local cluster 708. If so, the particulars of that are shared in a comparables report 738. The outlier selector 734 forwards a message 740 to the "P" input of the second comparator 730.

If the second comparator 730 finds a match for outlier 732 in the comparables report 738, an "=" output 742 will be output to indicate no fraud on comparing the odd bit of profile to similar things experienced by others in the local cluster 708.

Otherwise, a binary fraud flag or variable fraud score 744 will be output by the "not=" output 744. The details of the exception would also be useful to report.

Figure 8:
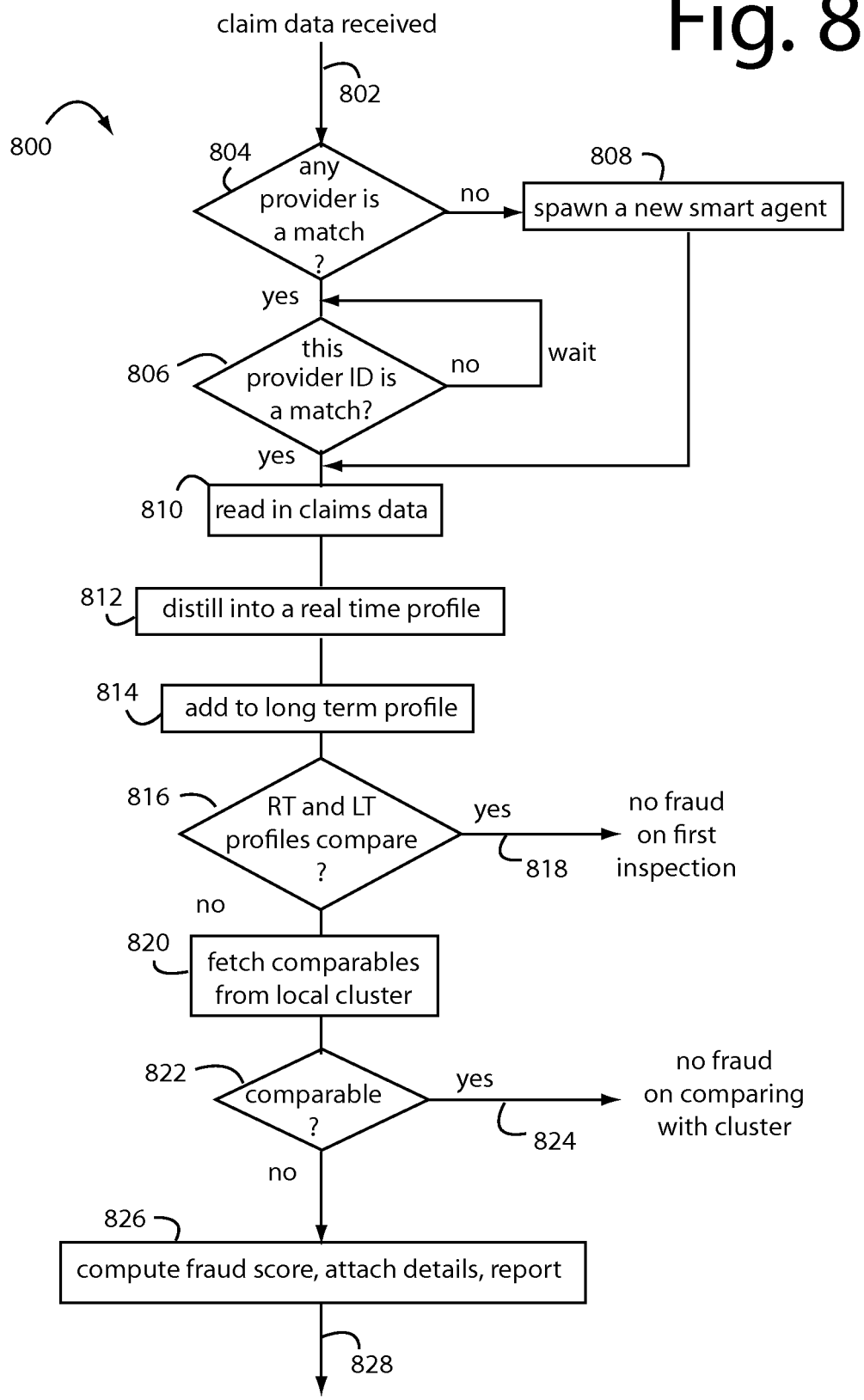
FIG. 8 is a flowchart diagram representing how a medical healthcare fraud smart agent can be implemented in software.

FIG. 8 represents a software-as-a-service implementation of a smart agent 800 in one embodiment of the present invention. It is a more practical, and run-time scalable implementation compared to hardware. A least one smart agent 800 must automatically spawn or be assigned for each individual healthcare provider subject to fraud monitoring. This implies automatic scaling up to thousands, or even millions of such smart agents 800 in one application.

Smart agents 800 are in a position in the network to receive streams of claims data 802. A step 804 tests whether any smart agent exists to handle the healthcare provider reporting. If yes, a step 806 checks if this smart agent is a match to the healthcare provider who is reporting. If not, it waits.

If the claims data coming in wasn't a match to any smart agent, then a step 808 spawns one for it.

A step 810 reads in the claims data. A step 812 distills it into real time (RT) profile data. The RT profile data is added to a long term (LT) profile data in a step 814. A step 816 compares the RT and LT profile data. If there is a match, a "no-fraud on first inspection" 818 is output.

Otherwise, comparables are fetched from a local cluster in a step 820. A step 822 tests if those find match to what is happening in real time. If yes, a "no fraud on comparing with cluster" out 824 results.

If not, a fraud has apparently been detected and a step 826 builds a report out 828 for a user to leverage in an investigation.

Figure 9:
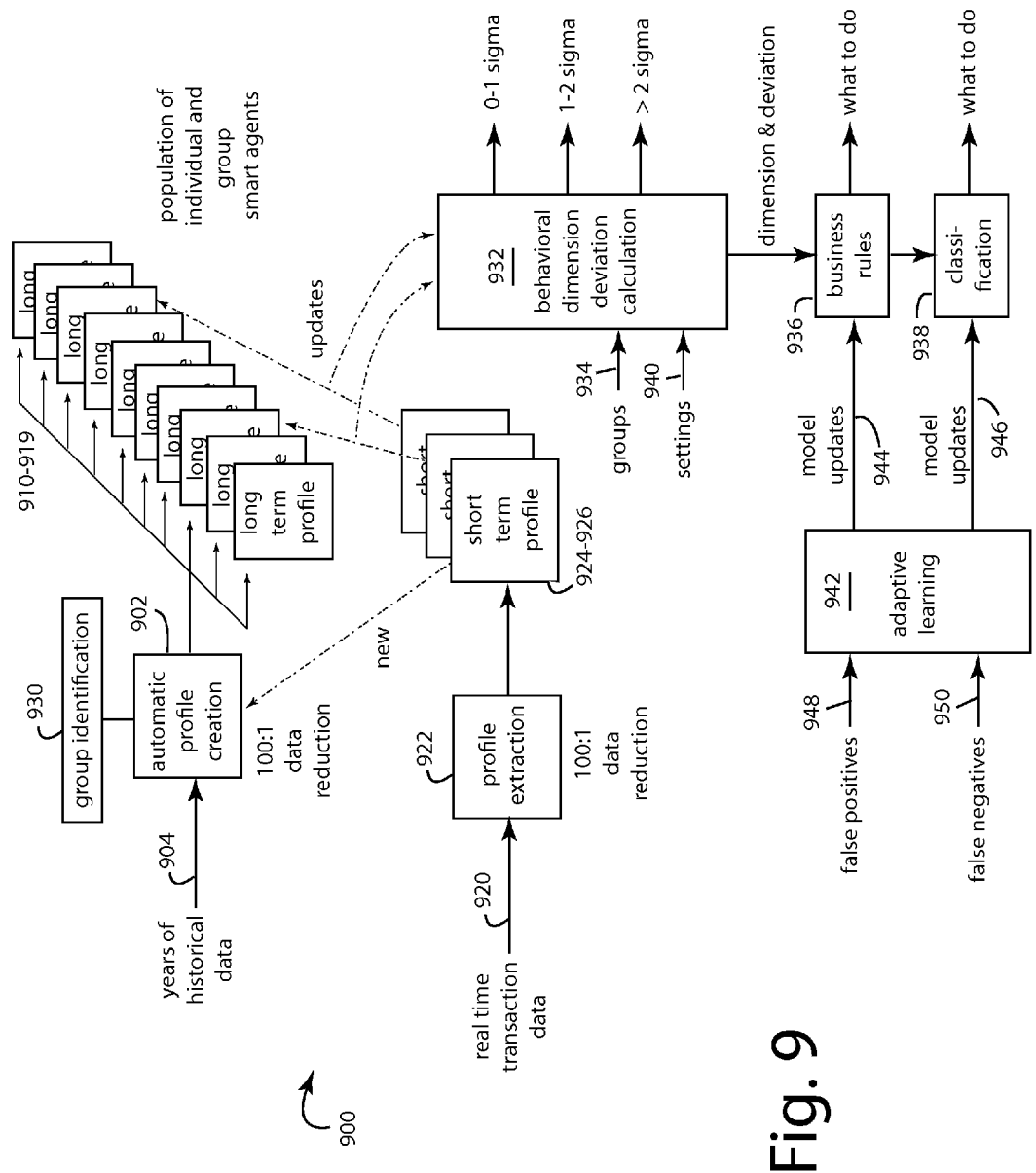
FIG. 9 is a functional block diagram representing a smart-agent based adaptive method for fraud detection.

FIG. 9 represents a smart-agent based adaptive method for fraud detection, and is referred to herein by the general reference numeral 900. Method 900 includes a step 902 for automatic profile creation. A historical data feed 904 of supervised learning data is sorted and searched to identify individual health care healthcare providers 910-919 using data mining techniques. A typical application will involve two years' worth of historical data 904 provided from millions of healthcare providers represented in long term profiles 910-919. Such historical data 904 could easily amount to twenty-seven terabytes of information, making it impractical to store here.

Embodiments of the present invention distill historical data 904 and real-time claims data 920 into behavioral profiles for as much as a 100:1 compression. A profile extraction step 922 operates on incoming real-time claims data 920 to build short-term profiles 924-926. Some of these short-term profiles 924-926 will be new, not having appeared in the historical data 904, and will be forwarded to automatic profile creation step 902. Others will have matches already existing in the population of individual health care healthcare providers 910-919.

Particular behavioral dimensions in long-term profiles 910-919 will match those in others. Such clustering can be used to judge if an unusual behavior for an individual is nevertheless normal for members of their group.

A group identification step 930 will collect these matching long-term profiles 910-919 and generate a group profile. These group profiles are added to the population of long-term profiles 910-919. For example, particular healthcare providers can share service locations, staffing practices, claim types, billing levels, etc. These commonalities would compel certain behaviors in all of the members, if only occasionally.

Short-term profiles 924-926 are used dimension-by-dimension to update the behaviors being tracked and followed by long-term profiles 910-919. Updates that deviate less than one sigma from that already stored as normal behavior will cause little of no concern.

A deviation calculation step 932 can also indicate updates that deviate more than one sigma but less than two sigma from that already stored as normal behavior. Such indicates marginal confidence of normal, non-fraudulent behavior, but needs further analysis and input from group profiles 934, business rules 936, or model classifiers 938. A settings input 940 can be used to change the confidence level thresholds.

Deviation calculation step 932 can also indicate updates that deviate more than two sigma from that already stored as normal behavior. Such indicates fraudulent behavior and requires the attention of auditors or law enforcement. The business rules 936 are adjusted to output commands on what-to-do in each case.

An adaptive learning step 942 computes the model updates 944 and 946 that are necessitated by false positives 948 and false negatives 950 to business rules 936 and classification models 938. Such classification models 938 include decision trees, neural networks, and genetic algorithms.

Each profile includes constituent behavioral dimensions that correspond to some significant aspect of the claim or transaction data that reflects the way the particular healthcare provider bills or provides services. These behavioral dimensions are carefully chosen to include only behavioral measures that correlate to fraud. Irrelevant details and categories can be skipped over. All profiles are provisioned with the same sets of behavioral dimensions so they can be consistently compared to one another.

In some embodiments of the present invention, each behavioral dimension is a single value representing the running average of all the training data and all the updates for that aspect of that smart agent profile. All the preceding individual data points and updates that contributed are disposed of, rather than retained after they have been used to calculate the rolling average. The memory demands of such a system would be very practical, e.g., a gigabyte to track one million smart agent profiles.

A rolling weighted average could also be used to give favor to the more recent updates, for example. A time series can be used to smooth out short term fluctuations. Simple moving averages, cumulative moving averages, weighted moving averages, exponential moving averages can be mixed amongst different aspects, depending on experience with false positives and false negatives.

In summary, embodiments of the present invention excel in fraud detection in hundreds of very different industry applications because millions of smart agent profiles can be spawned to track millions of credit cards, millions of healthcare providers, millions of taxpayers, etc. Each smart agent profile adapts itself to its corresponding target, learning and changing over time independently of all the others. Tighter controls can be used because the controls are customizable, not one-size-fits-all.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. An adaptive, electronic, computer implemented, and smart agent based method for healthcare claim fraud detection, comprising:
   a data reduction step for electronically converting claim data into profile data comprising a plurality of behavioral dimensions, wherein a minimum of a hundred fold reduction in data volume is realized without needing to retain historical claim data;
   an individual recognition step for identifying individual healthcare providers in said profile data and for collecting such into corresponding long term individual healthcare provider profiles;
   a clustering step for identifying groups of healthcare providers in said profile data and for collecting such into respective long term group profiles;
   a smart agent building step for feeding historical claim data through the data reduction step to the individual recognition step and the group recognition step, and for creating a plurality of individual and group smart agents therefrom and each including profile data organized into said plurality of behavioral dimensions;
   an updating step for using claim data fed through the data reduction step to be added to any matching long term individual healthcare provider profile;
   a real time fraud detection step for comparing updates of individual ones of the plurality of behavioral dimensions to their running values in the long term individual healthcare provider profiles and measuring any significant deviations;
   a fraud classification step for scoring said deviations as being the result of fraudulent or non-fraudulent behavior on the part of the respective individual healthcare provider having sourced the claim data;
   wherein, the step of updating produces a self-learning and adaptive fraud detection capability that evolves over time healthcare provider-by-healthcare provider.

2. The method of claim 1, further comprising:
   a non-fraudulent classification step for dividing score determinations of non-fraudulent behavior into ones requiring and not requiring further investigation.

3. The method of claim 1, further comprising:
   a group classification step for comparing updates of individual ones of the plurality of behavioral dimensions to their running values in related long term group healthcare provider profiles, and for measuring any significant deviations from other members in the group.

4. The method of claim 1, wherein:
   each of the plurality of behavioral dimensions maintained by each of the plurality of individual and group smart agents comprises a single computed value representing an average of the training data and updates received, said average representing at any moment the most current running estimate of what represents normal, non-fraudulent behavior for that aspect.

5. The method of claim 1, further comprising:
   a clustering step for creating group profiles from unsupervised training data.

* * * * *